US009724044B2

(12) United States Patent
Mayer et al.

(10) Patent No.: US 9,724,044 B2
(45) Date of Patent: Aug. 8, 2017

(54) DEVICE TO BE IMPLANTED IN A HUMAN OR ANIMAL BODY FOR MATERIAL OR SIGNAL DELIVERY OR ACQUISITION WITHIN THE BODY, AND METHOD OF IMPLANTING THE DEVICE

(71) Applicant: WOODWELDING AG, Stansstad (CH)

(72) Inventors: Jörg Mayer, Niederlenz (CH); Barbara Froesch, Mettmenstetten (CH); Mario Lehmann, Les Pommerats (CH); Jens Langhoff, Zurich (CH); Thomas Knecht, Hausen (CH); Stephanie Mehl, Zug (CH); Andrea Mueller, Winterhur (CH)

(73) Assignee: WOODWELDING AG, Stansstad (CH)

( * ) Notice: Subject to any disclaimer, the term of this patent is extended or adjusted under 35 U.S.C. 154(b) by 123 days.

(21) Appl. No.: 14/665,195

(22) Filed: Mar. 23, 2015

(65) Prior Publication Data
US 2015/0196253 A1   Jul. 16, 2015

Related U.S. Application Data

(60) Division of application No. 12/907,611, filed on Oct. 19, 2010, now Pat. No. 9,005,184, which is a
(Continued)

(51) Int. Cl.
*A61B 17/68* (2006.01)
*A61B 5/00* (2006.01)
(Continued)

(52) U.S. Cl.
CPC ............ *A61B 5/6878* (2013.01); *A61B 5/076* (2013.01); *A61B 5/4839* (2013.01); *A61B 17/68* (2013.01);
(Continued)

(58) Field of Classification Search
CPC .............. A61B 17/3472; A61B 17/68; A61B 2017/00955; A61B 2017/8655; A61B 5/6878; A61F 2002/2839
(Continued)

(56) References Cited

U.S. PATENT DOCUMENTS 6,214,008 B1   4/2001   Illi
6,579,533 B1   6/2003   Tormala et al.
(Continued)

FOREIGN PATENT DOCUMENTS

EP   2 596 764   5/2013
JP   H11-504231   4/1999
(Continued)

OTHER PUBLICATIONS

U.S. Appl. No. 61/386,160, filed Sep. 24, 2010. Inventor: Mueller.

*Primary Examiner* — Kevin C Sirmons
*Assistant Examiner* — Deanna K Hall
(74) *Attorney, Agent, or Firm* — Rankin, Hill & Clark LLP

(57) ABSTRACT

For fixedly implanting a device for material or signal delivery or acquisition or a part of such a device in a human or animal body, an opening is provided in hard tissue of the body, the opening reaching through a hard tissue layer, e.g. through a cortical bone layer into cancellous bone underneath. The device includes a plug portion and/or a cover portion which includes a ring of a material having thermoplastic properties extending around the plug portion or on a tissue facing surface of the cover portion. The opening provided in the hard tissue has a cross section at least in the area of its mouth that is adapted to the plug or cover portion such that the plug portion can be introduced through the mouth of the opening or the cover portion can be positioned over the mouth of the opening such that the ring extends
(Continued)

around the opening, along its wall and/or on the hard tissue surface around its mouth.

8 Claims, 9 Drawing Sheets

Related U.S. Application Data continuation-in-part of application No. PCT/CH2010/000217, filed on Sep. 7, 2010.

(60) Provisional application No. 61/241,184, filed on Sep. 10, 2009.

(51) Int. Cl.

| | | |
|---|---|---|
| *A61B 5/07* | (2006.01) | |
| *A61D 7/00* | (2006.01) | |
| *A61N 7/00* | (2006.01) | |
| *A61B 90/90* | (2016.01) | |
| *A61B 90/98* | (2016.01) | |
| *A61B 17/34* | (2006.01) | |
| *A61B 17/00* | (2006.01) | |
| *A61B 17/56* | (2006.01) | |
| *A61B 17/86* | (2006.01) | |
| *A61F 2/30* | (2006.01) | |
| *A61F 2/28* | (2006.01) | |

(52) U.S. Cl.
CPC .............. *A61B 90/90* (2016.02); *A61B 90/98* (2016.02); *A61D 7/00* (2013.01); *A61N 7/00* (2013.01); *A61B 17/3472* (2013.01); *A61B 2017/00955* (2013.01); *A61B 2017/561* (2013.01); *A61B 2017/8655* (2013.01); *A61B 2503/40* (2013.01); *A61B 2562/164* (2013.01); *A61F 2/30744* (2013.01); *A61F 2002/2839* (2013.01); *A61N 2007/0047* (2013.01)

(58) Field of Classification Search
USPC ........................................................ 606/300
See application file for complete search history.

(56) References Cited

U.S. PATENT DOCUMENTS

| | | |
|---|---|---|
| 6,620,185 B1 | 9/2003 | Harvie et al. |
| 6,936,270 B2 | 8/2005 | Watson et al. |
| 7,008,226 B2 | 3/2006 | Mayer et al. |
| 7,144,414 B2 | 12/2006 | Harvie et al. |
| 7,335,205 B2 | 2/2008 | Aeschlimann et al. |
| 7,785,347 B2 | 8/2010 | Harvie et al. |
| 8,066,712 B2 * | 11/2011 | Truckai .............. A61B 17/8811 606/92 |
| 2001/0021852 A1 | 9/2001 | Chappius |
| 2005/0112091 A1 | 5/2005 | DiMauro et al. |
| 2006/0105295 A1 * | 5/2006 | Mayer .................... A61B 17/68 433/173 |
| 2007/0083265 A1 | 4/2007 | Malone |
| 2008/0109080 A1 | 5/2008 | Aeschlimann et al. |
| 2008/0269649 A1 | 10/2008 | Dorawa |
| 2009/0131947 A1 | 5/2009 | Aeschlimann et al. |
| 2012/0239049 A1 | 9/2012 | Truckai et al. |
| 2012/0259373 A1 | 10/2012 | Dehnad et al. |

FOREIGN PATENT DOCUMENTS

| | | |
|---|---|---|
| JP | 2004-520908 | 7/2004 |
| WO | 02/098307 | 12/2002 |
| WO | 2008/034276 | 3/2008 |
| WO | 2008/128367 | 10/2008 |
| WO | 2009/109057 | 9/2009 |

* cited by examiner

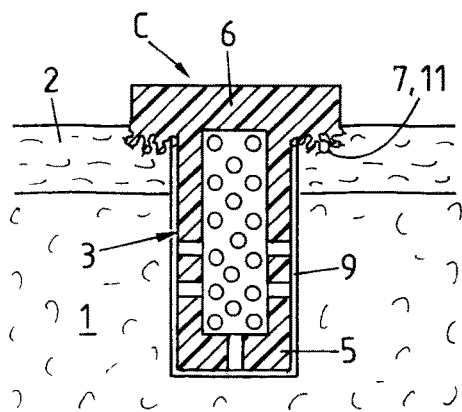
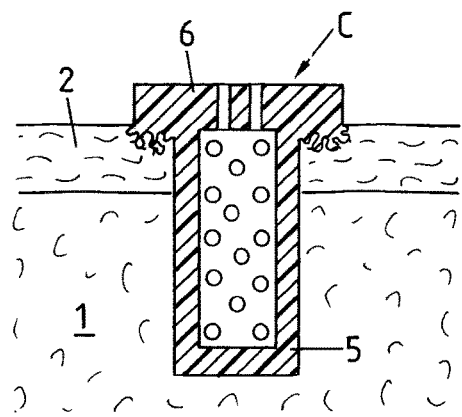
Fig. 5   Fig. 6
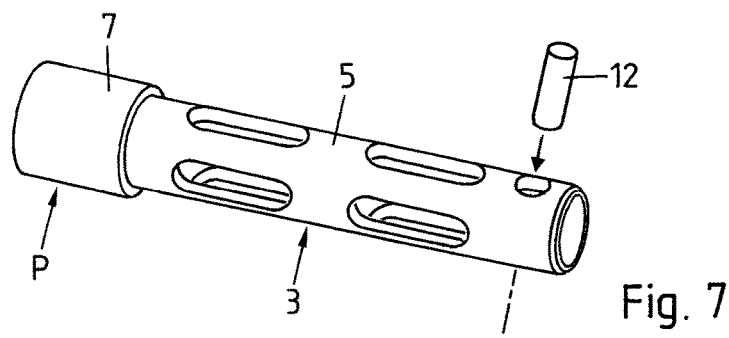
Fig. 7
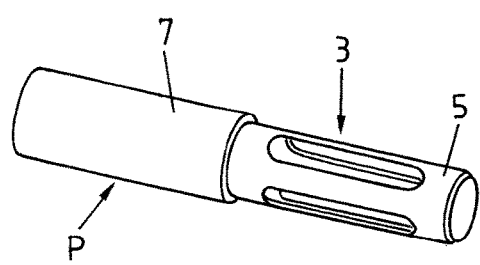
Fig. 8

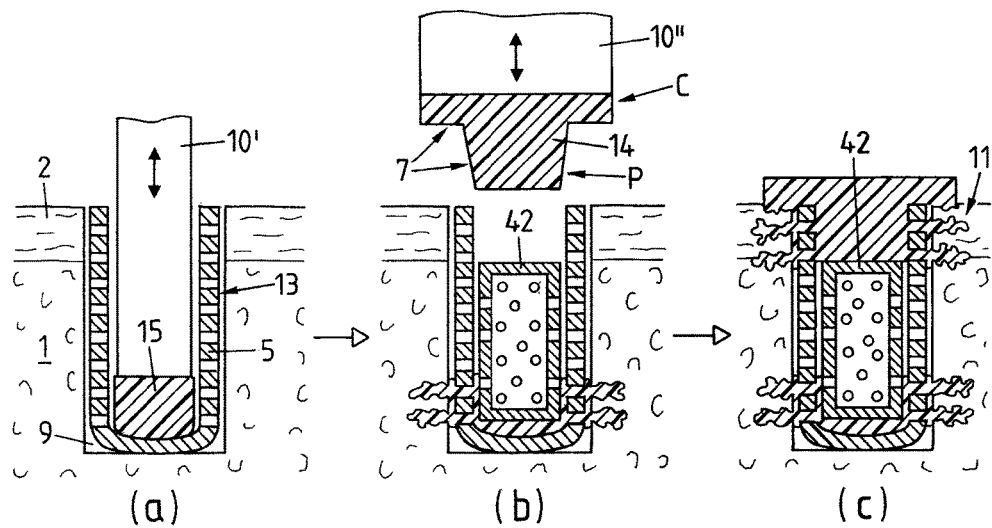
Fig. 15
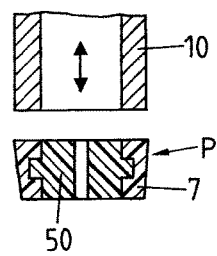
Fig. 16
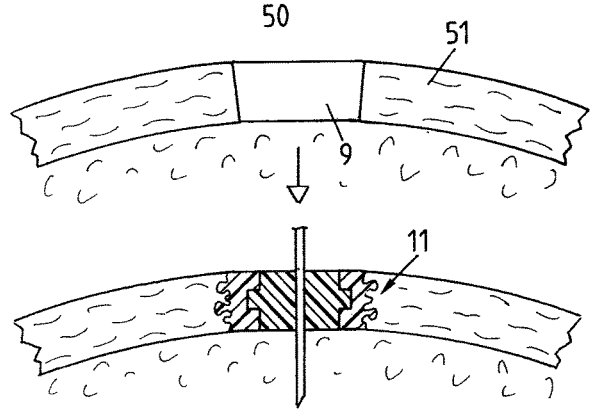

DEVICE TO BE IMPLANTED IN A HUMAN OR ANIMAL BODY FOR MATERIAL OR SIGNAL DELIVERY OR ACQUISITION WITHIN THE BODY, AND METHOD OF IMPLANTING THE DEVICE

CONTINUITY

This application is a divisional of Ser. No. 12/907,611 filed Oct. 19, 2010, which is a continuation-in-part of PCT/CH2010/000217, filed on Sep. 7, 2010 and currently pending, which claims priority of U.S. application 61/241,184, filed on Sep. 10, 2009.

BACKGROUND OF THE INVENTION

Field of the Invention

The invention is in the field of medical technology and relates to a device of which at least a part is suitable for being implanted in a human or animal body and which is equipped for material or signal delivery or acquisition within the body. The invention also concerns methods for implanting the named implantable devices or implantable device parts.

Description of Related Art

Devices for material delivery within a body are in particular drug delivery devices (delivering therapeutically or prophylactically active molecules or particles into tissue) and infusion devices but may also serve for delivering other materials such as e.g. contrast agents or fluorescent molecules, viable cells (e.g. for differentiation and integration in the tissue or for production of a desired protein) or subatomic particles (particle radiation) within the body. Devices for material acquisition within a body are e.g. catheters or hollow needles for removing tissue components or body fluids e.g. for therapeutic or diagnostic purposes. Devices for signal delivery within a body serve e.g. for stimulating tissue, for activating deposited chemicals, or for activating other implanted devices such as e.g. drug delivery devices, wherein the signals to be delivered within the body may be e.g. electric, mechanic, acoustic or optic signals. Devices for signal acquisition within a body serve e.g. diagnostic purposes, wherein the signal acquisition may comprise e.g. acquisition of signals transmitted into tissue, measuring a local body temperature, pressure, or chemistry, or sensing the state of another implanted device such as e.g. a drug delivery device.

Devices for material or signal delivery or acquisition within a body may also be equipped for combinations of the above named functions such as e.g. a combination of signal delivery and signal acquisition for diagnostic (e.g. scanning) purposes or a combination of a drug delivery function combined with a signal acquisition function for detecting a need for delivery in the concerned tissue and a signal delivery function for activation of the drug delivery function. In many cases the named devices comprise electronic or microelectric and/or micromechanic elements. The devices may be fully implanted or they may comprise parts to be implanted and parts which are situated outside of the body, wherein the implanted parts are physically or functionally connected or connectable to the non-implanted parts, and wherein for such cases the invention concerns the implanted device part only. Examples for such only partly implanted devices are e.g. devices comprising an implanted catheter and non-implanted reservoir and drive means, devices comprising an implanted sensor and a non-implanted device part for registration of the sensor readings, or systems comprising an implanted identification chip (RFID) and a non implanted reading device.

The term "device for implantation in a human or animal body for material or signal delivery or acquisition" as used in connection with the present invention is understood to comprise all the above named groups and examples of implantable devices or implantable device parts and all devices and device parts which one skilled in the art will subsume under the named groups.

Implantable drug delivery devices are well known in today's medicine. Such drug delivery devices are usually designed for sustained and/or delayed release of the drug, wherein the delivery process may be controlled by chemical characteristics of the device (e.g. biological resorption of device components enclosing the drug), by control means, which are e.g. integrated in the device to activate the delivery either fully automatically or through signals or actions initiated from outside of the body.

The known implantable drug delivery devices as well as other known implantable devices for material or signal delivery or acquisition such as implantable devices comprising electronic or microelectric and/or micromechanic elements (e.g. RFID-chips, sensors, cardiac pulse generators, electric or mechanic elements for activating delivery devices) are implanted to be either "floating" (e.g. subcutaneously implanted) or to be fixed in a specific body location (e.g. by being tied to soft tissue with suture or wire or by being fixed to hard tissue with the aid of a bone anchor with or without suture). Floating implantation is in particular known for RFID-chips (e.g. for identification of animals) and for drug delivery devices. Fixed implantation is more involved but in many cases advantageous as it prevents migration of the device in the body. Regarding drug delivery, fixed implantation is particularly advantageous if the drug is to be administered locally, wherein the fixation location is chosen to coincide as closely as possible with the location of the desired administration.

Drug delivery devices suitable for fixed implantation in bone tissue are e.g. described in the publication U.S. Pat. No. 6,936,270. The described devices comprise an e.g. metallic osteosynthesis element such as a bone screw, bone nail or bone staple to be at least partly embedded in the bone tissue. The drug and possibly a suitable drug carrier is contained in the screw or nail head or in a container fixed to the middle section of the staple and the head or container is designed for delivery of the drug to tissue or body fluid situated adjacent to the bone in which the device is anchored. The devices are said to be particularly suited for implantation within a synovial joint and for delivering a drug into the synovial fluid of the joint.

Also known (e.g. WO 2005/053795) are drug delivery devices in the form of cannulated bone screws comprising openings connecting the axial screw channel with the threaded screw surface and containing the drug to be delivered in the channel, the drug being delivered through the openings to the bone tissue in which the screw is embedded.

Implantable drug delivery devices comprising an osteosynthesis element (e.g. bone screws or plates) being made of a biodegradable material are described e.g. in the publication U.S. Pat. No. 6,214,008. According to this publication, the drug (e.g. growth factor GF or bone morphogenic protein BMP) is integrated in the biodegradable material of the osteosynthesis element and is released with a rate directly dependent on the degradation rate of the biodegradable material. The devices are said to be particularly advantageous for delivering the drugs to bone defect locations, e.g. to a fractured bone tissue, for furthering bone repair.

For the above mentioned known drug delivery devices designed for fixed implantation in bone tissue, the fixation of the device is usually coupled with producing a bone defect, i.e. an opening in the bone tissue originating from a bone surface (accessible bone surface) and usually penetrating a cortical bone layer to reach into the cancellous bone tissue situated beneath the cortical bone layer. This means that the opening, even if it is only small, constitutes a non-natural passage from a first body region (on the accessible side of e.g. the cortical bone layer) to a second body region (on the non-accessible side of e.g. the cortical bone layer), wherein characteristics, functions and needs of the two body regions may differ considerably, and wherein, before the opening was provided, the two body regions were naturally and appropriately sealingly separated from each other by e.g. the cortical bone layer. It is known that bone screws, bone nails or bone staples implanted in such openings are not capable of mending the natural barrier function of the cortical bone layer completely. Chemicals and even bacteria will be able to pass through the impaired cortical bone layer along the device surface, in particular when an initial press fit has relaxed or, in the case of bioresorbable devices, when resorption has started. This means that the above shortly described known drug delivery devices, when fixed to or in bone not only constitute a possibly undesired impairment of a natural barrier function of the cortical bone layer but also are not able to fully limit delivery of the drug to one side of the cortical bone layer, even if they are designed specifically for such a purpose (delivery to accessible side of cortical layer according to U.S. Pat. No. 6,936,270 or delivery to non-accessible side of cortical layer according to WO 2005/053795 or U.S. Pat. No. 6,214,008).

BRIEF SUMMARY OF THE INVENTION

It is an object of the present invention to provide a further device for material or signal delivery or acquisition within a human or animal body, the device or part thereof being suitable for fixed implantation in hard tissue of the human or animal body or in a corresponding replacement material situated in the human or animal body. It is also an object of the present invention to provide a method for implanting the device or part thereof. One particular improvement which can be achieved by using the device and method according to the invention concerns their ability to reconstitute the natural barrier function of a hard tissue layer, in particular of a bone layer, which is to be penetrated on implantation of the device or device part.

It is a further object of the present invention to provide a drug delivery implant that is capable of ensuring an improved specificity of the body location and/or of the body tissue to which the drug is delivered. It is yet another object of the present invention to provide an implantation method for a drug delivery implant with improved specificity of the location and/or of the tissue to which the drug is delivered. This means e.g. that the invention is to make it possible to fixate a drug delivery device in or on hard tissue, in particular bone tissue, wherein the fixation comprises penetration of a hard tissue layer and wherein in spite of such penetration the drug delivery is limited to a much higher degree than possible according to the state of the art, to only one side of this hard tissue layer.

It is an even a further object of the present invention to provide a surgical method that includes implanting a drug delivery device for the purpose of promoting tissue healing at a site where a soft tissue/soft tissue replacement material is attached to hard tissue/hard tissue replacement material.

These and other objects are achieved by the invention as defined in the claims.

The invention is mainly based on the finding that liquefied thermoplastic material brought into contact with hard tissue or a corresponding replacement material not only easily penetrates pores and openings of the hard tissue or replacement material to constitute, on re-solidification, a positive fit connection therewith, but in addition is capable of contacting the hard tissue or replacement material in a very intimate manner such that on re-solidification the contact area constitutes a tight seal. In particular, it is found that the sealing capability of the named contact area is far better and considerably less prone to deterioration due to loading than the sealing capability of the above named devices according to the state of the art, mainly bone screws being screwed into a hard tissue opening or bone nails or staples being impacted into the hard tissue.

According to an aspect of the invention, the implantable device for material or signal delivery or acquisition or the implantable part of such a device comprises a plug portion and/or a cover portion and a material or signal delivery or acquisition portion wherein the plug or cover portion are attached or attachable to each other or fully separate from each other. The plug or cover portion comprises a material having thermoplastic properties, which is situated around the plug portion and/or on the hard tissue facing side of the cover portion constituting by itself a preferably complete ring or constituting at least part of a ring arranged in a ring-shaped groove and protruding therefrom.

For implanting the device according to the aspect of the invention, an opening is provided in the hard tissue or replacement material, the opening reaching through a hard tissue layer from an accessible side to a non-accessible side thereof. A cross section of at least a mouth region of the opening is adapted to the plug or cover portion of the device or device part. The device or device part is then positioned relative to the hard tissue opening such that the ring of material having thermoplastic properties or the groove containing such material extends all around the opening, along the inside wall of the opening and/or along the hard tissue surface around the mouth of the opening.

At least part of the thermoplastic material is then liquefied and made to get into contact with the inside wall of the opening or the hard tissue surface around the mouth of the opening (if applicable, simultaneously flowing along the groove to form a complete ring), advantageously combined with making the liquefied material to penetrate into cavities or pores of the hard tissue. The liquefied material then re-solidifies to constitute a sealing ring being anchored in the hard tissue or replacement material and extending all around the opening along the inside wall of the opening (ring around plug portion) and/or along the hard tissue surface around the mouth of the opening (ring on cover portion) and therewith to constitute a sealing connection or sealing ring between the liquefiable material and the hard tissue or replacement material or preferably a combination of a sealing connection and a positive fit connection therebetween.

Instead of implantation of the device or device part in a hard tissue opening, which is specifically made for such implantation, it is possible also, to implant the device or device part in a hard tissue opening caused by other circumstances (e.g. bone fracture, removal of bone tumor, pockets caused by periodontitis), wherein the implant is chosen to fit into the opening in the way as described above for a specifically provided opening and wherein the sealing ring achieved during the implantation may provide a sealing not only between the device or device part and bone tissue but possibly also between the device or device part and other tissue or other implant which may be implanted beforehand or afterwards.

The in situ liquefaction of the material having thermoplastic properties is achieved by transmitting energy to the ring or part ring of material having thermoplastic properties, preferably vibrational energy (in particular ultrasonic vibration energy) being transmitted to the thermoplastic material possibly via other portions of the device or device part from e.g. a correspondingly shaped sonotrode of an ultrasonic device. Therein the device or device part may be temporarily attached to the sonotrode or the sonotrode may be pressed against a proximal face of the device or device part. However, it is possible also to achieve the desired liquefaction e.g. with the aid of laser light being absorbed in the thermoplastic material to form the sealing ring or in a device area adjacent to this material or with the aid of resistive or inductive heating of the thermoplastic material or an adjacent device area.

The sealing ring produced by implanting the device according to the aspect of the invention may be circular and extend in a substantially even plane or it may have any other form (e.g. polygonal, oval, irregular and/or extending in a non-even plane). The material having thermoplastic properties constituting the sealing ring may be non-bioresorbable or bioresorbable, wherein the character of the resorbability may need to be adapted to a desired delivery or acquisition characteristic and/or to expected tissue regeneration. Instead of being implanted through a hard tissue layer having a natural sealing function as e.g. through a cortical bone layer, the device according to the invention may also be implanted in hard tissue without such a function, e.g. in cancellous bone tissue made accessible e.g. by other surgery, wherein in such a case the sealing function of the sealing ring is of a very minor importance.

The plug portion, the cover portion or a combination of plug and cover portion may constitute the whole implantable device or device part. Alternatively, the plug portion, cover portion or combination of the two may carry further portions wherein these further portions may extend from the plug or cover portion distally or proximally and may be attached to the plug or cover portion before or after liquefaction and re-solidification of the liquefiable material comprised by the plug or cover portion. The ring or part ring of the material having thermoplastic properties may constitute a body of this material which is suitably attached to further portions e.g. of non-liquefiable material (e.g. arranged in a groove of such other portions and protruding from the groove) or it may constitute a region of a non ring-shaped device portion, e.g. of a cylindrical or conical plug portion or of a plate shaped cover portion, which fully consist of the material having thermoplastic properties.

One of many applications of above-discussed aspect of the invention is support of tendon or ligament repair by local delivery of a bone growth factor near the tendon/bone or ligament/bone interface. The bone growth factor may be of the Bone Morphogenic Protein family (BMP 2, 6, 7, 12, 13)/the transforming growth factor beta family, an Insulin Growth Factor (e.g. IGF 1), a Platelet Derived Growth Factor (PDGF), a Growth and Differentiation Factor (e.g. GDF 5) etc. and also a combination thereof and/or other an other drug including a non-proteinaceous drug including small molecules (e.g. biphosphonates), and/or anti-inflammatory and/or antibiotic drugs possibly in combination with a proteinaceous drug, etc.

In accordance with an other, second aspect of the invention, a surgical method of fastening soft tissue and/or soft tissue replacement material to hard tissue and/or hard tissue replacement material is provided, the method comprising fastening the soft tissue/soft tissue replacement material to the hard tissue/hard tissue replacement material using a fastener implanting a device comprising surface regions of a material having thermoplastic properties and being liquefiable through application of energy to the device, wherein the device is equipped for causing at least part of the material having thermoplastic properties to liquefy and to bring the material into contact with the hard tissue/hard tissue replacement material to form on re-solidification an anchor in the hard tissue/hard tissue replacement material, the device further comprising a drug promoting healing, wherein the device is implanted near the interface between the soft tissue/soft tissue replacement material and the hard tissue/hard tissue replacement material.

"Near the interface" means at the interface or in a vicinity thereof. "At the interface" means, for example, that the further device is implanted where the soft tissue is to be in physical contact with the hard tissue/replacement material. For example, the device may be implanted so that a proximal surface is approximately flush with the hard tissue/replacement material surface and the soft tissue/replacement material covers the device at least partially. "In a vicinity of the interface" may mean that the device is not in physical contact with the soft tissue but is close enough to ensure that the enhanced concentration of released drug near the device causes a diagnosable/discernible enhancement effect on the tissue healing at the interface.

If the device is a device according to the first aspect, the sealing ring may be distal of a location at which the drug may be released to the tissue so that the drug is released towards the tissue adjacent the cortical bone and prevented from getting into an interior of the bone. Alternatively, the sealing ring may be proximal of a location at which the drug may be released to the tissue so that the drug is released towards the bone tissue and prevented from getting into the tissue adjacent the bone. As yet another alternative, drug releasing locations may be present on both sides of the sealing ring. As an even further alternative, the device may be different from a device according to the first aspect in that not a complete sealing ring is formed.

Embodiments that comprise releasing the substance towards the tissue adjacent the bone (the soft tissue) may be advantageous in that mutual engraftment of the hard and soft tissues (and/or replacement materials) is achieved, for example engraftment of bone and ligament/tendon tissue. Embodiments that comprise releasing the substance into the bone may be advantageous in situations where the bone tissue has to heal and/or to be strengthened.

In embodiments of the second aspect of the invention, the fastener or at least one of a plurality of fasteners may be at least one of:

a fastener that comprises material liquefiable by the impact of energy and that is implanted by liquefying at least a portion of the material, pressing a liquefied portion of the material into the hard tissue/replacement material and letting the liquefied portion re-solidify to provide an anchoring. For example, this may be achieved by the method as described in any one of the publications: U.S. Pat. Nos. 7,335,205, 7,008,226, US 2006/105295, US-2008/109080, and US 2009/131947, incorporated herein by reference in their entirety.

A suture that is anchored by a suture anchor, wherein the suture anchor comprises material liquefiable by the impact of energy and that is implanted by liquefying at least a portion of the material, pressing a liquefied portion of the material into the hard tissue/replacement material and letting the liquefied portion re-solidify to provide an anchoring. For example, this may be achieved by the method as described in any one of the publications: U.S. Pat. Nos. 7,335,205, 7,008,226, US 2006/105295, US-2008/109080, and US 2009/131947, incorporated herein by reference in their entirety.

A fastener (for example for 'gluing') such as an adhesive and/or an artificial tissue or absorbable material temporarily fastening the soft tissue/soft tissue replacement material to the hard tissue/hard tissue replacement material In this, the suture may be secured to the suture anchor at any time, i.e. prior to the anchoring, during the anchoring, and/or thereafter.

In any embodiment that comprises using a suture anchor to fasten soft tissue/replacement material to hard tissue/replacement material, the suture anchor may be an anchor as described in U.S. 61/386,160, incorporated herein by reference in its entirety. It may be anchored using a device and/or a method as described in U.S. 61/386,160. Especially, it may be a suture anchor comprising a pin portion and a material having thermoplastic properties being arranged at least partly around a pin portion circumference, and, for locking the suture on implantation, further comprising a suture groove extending in an axial direction along the pin portion and having a zero depth portion at a proximal end of the pin portion, or a collapsible plurality of eyelets at a distal end of the pin portion. Alternatively, it may be a suture anchor as described in WO 2009/109057/U.S. patent application Ser. No. 12/920,696 also incorporated herein by reference.

As already mentioned, it is preferred to liquefy the material having thermoplastic properties by applying vibrational energy, in particular ultrasonic vibration energy. This method corresponds with the per se known implantation technique according to which an implant comprising a material having thermoplastic properties and being liquefiable by mechanical vibration is anchored in hard tissue, in particular in bone tissue, by applying such vibration to the implant, in particular ultrasonic vibration. Such implantation techniques are disclosed e.g. in the publications U.S. Pat. Nos. 7,335,205, 7,008,226, US 2006/105295, US-2008/109080, and US 2009/131947. The whole disclosure of all the named publications is enclosed herein by reference.

The basis of the above named implantation techniques is the in situ liquefaction of a thermoplastic material having mechanical properties suitable for a mechanically satisfactory anchorage of the implant in the bone tissue, wherein the material in its liquefied state has a viscosity which enables it to penetrate into natural or beforehand provided pores, cavities or other structures of the bone tissue, and wherein an only relatively small amount of the material is liquefied such that a non-acceptable thermal load on the tissue is prevented. When re-solidified, the thermoplastic material which has penetrated into the pores, cavities or other structures constitutes a positive fit connection with the bone tissue. Of course such positive fit connection can also be achieved in other suitably hard material of a suitable structure or form such as e.g. porous bone replacement material or further implants, or simultaneously in both bone tissue and other materials situated adjacent to the bone tissue.

Suitable liquefaction combined with an acceptable thermal loading of the tissue and suitable mechanical properties of the positive fit connection is achievable by using materials with thermoplastic properties having a modulus of elasticity of at least 0.5 GPa and a melting temperature of up to about 350° C. and by providing such material e.g. on an implant surface, which on implantation is pressed against the bone tissue, preferably by introducing the implant in a bone opening which is slightly smaller than the implant or by expanding the implant in a bone opening which originally is slightly larger than the implant (expansion e.g. by mechanically compressing or buckling of the implant). During implantation, the implant is subjected to vibration of a frequency preferably in the range of between 2 and 200 kHz (preferably ultrasonic vibration) by applying e.g. the sonotrode of an ultrasonic device to the implant. Due to the relatively high modulus of elasticity the thermoplastic material is able to transmit the ultrasonic vibration with such little damping that inner liquefaction and thus destabilization of the implant does not occur, i.e. liquefaction occurs only where the liquefiable material is in contact with the bone tissue and is therewith easily controllable and can be kept to a minimum.

Instead of providing the liquefiable material on the surface of the implant (disclosed e.g. in U.S. Pat. Nos. 7,335,205 or 7,008,226), it is possible also to provide the liquefiable material in a perforated sheath and to liquefy it within the sheath and press it through the sheath perforations to the surface of the implant and into the pores or cavities of the bone tissue (disclosed e.g. in U.S. Pat. Nos. 7,335,205 and 7,008,226) and/or it is possible to liquefy the liquefiable material between two implant parts of which one is vibrated and the other one serves as counter element, the interface between the two implant parts being positioned as near as possible to the bone tissue (as disclosed in the publications US 2009/131947 and WO2009/109057).

Materials having thermoplastic properties suitable for the device and the method according to the invention are thermoplastic polymers, e.g.: resorbable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

Specific embodiments of degradable materials are Polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in CA Bailey et al., J Hand Surg [Br] 2006 April; 31(2):208-12.

Specific embodiments of non-degradable materials are: Polyetherketone (PEEK Optima, Grades 450 and 150, Invibio Ltd), Polyetherimide, Polyamide 12, Polyamide 11, Polyamide 6, Polyamide 66, Polycarbonate, Polymethylmethacrylate, Polyoxymethylene, or polycarbonateurethane (in particular Bionate by DSM). An overview table of polymers and applications is listed in Wintermantel, page 150; specific examples can be found in Wintermantel page 161 ff. (PE, Hostalen Gur 812, Hochst AG), pages 164 ft (PET) 169ff. (PA, namely PA 6 and PA 66), 171 ff. (PTFE), 173 ft (PMMA), 180 (PUR, see table), 186 ft (PEEK), 189 ft (PSU), 191 if (POM—Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g. of calcium phosphate ceramics or glasses) and such represent a composite material. The material having thermoplastic properties may further contain components which expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g. promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particlulate or molecular) which are capable of absorbing such radiation of a specific frequency range (in particular of the visible or infrared frequency range), e.g. calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseo-integration stimulating fillers that are only partially or hardly degradable, for non degradable polymers include: Bioglasses, Hydroxyapatite (>90% cristallinity), HAPEX®, see SM Rea et al., J Mater Sci Mater Med. 2004 September; 15(9):997-1005; for hydroxyapatite see also L. Fang et al., Biomaterials 2006 July; 27(20):3701-7, M. Huang et al., J Mater Sci Mater Med 2003 July; 14(7):655-60, and W. Bonfield and E. Tanner, Materials World 1997 January; 5 no. 1:18-20. Embodiments of bioactive fillers and their discussion can for example be found in X. Huang and X. Miao, J Biomater App. 2007 April; 21(4):351-74), JA Juhasz et al. Biomaterials, 2004 March; 25(6):949-55. Particulate filler types include: coarse type: 5-20 μm (contents, preferentially 10-25% by volume), submicron (nanofillers as from precipitation, preferentially plate like aspect ratio >10, 10-50 nm, contents 0.5 to 5% by volume).

Portions of the implantable device or device part which do not serve the anchoring and sealing function my consist of any suitable material/material combination (e.g. polymer, metal, ceramic, glass) which material may be bio-resorbable or not bio-resorbable and liquefiable or not liquefiable.

The devices and methods according to the invention are in particular suitable for minimally invasive surgery but are also applicable in open surgery.

Instead of for delivering material or signals to a human or animal body, it is possible also to use the device according to the aspect of the invention for delivering energy to tissue, in particular in the form of radiation (e.g. gamma-radiation, electromagnetic radiation such as e.g. infrared light).

BRIEF DESCRIPTION OF THE DRAWINGS

The invention is described in further detail in connection with the appended Figs., wherein:

FIGS. 5 and 6 show further embodiments of devices according to embodiments of the invention, the devices serving again for e.g. drug delivery on the non-accessible side (FIG. 5) or the accessible side (FIG. 6) of a hard tissue layer;

FIGS. 7 to 13 show further exemplary embodiments of the device according to embodiments of the invention, the devices again being equipped for e.g. drug delivery to the non-accessible side of a hard tissue layer through which the device is implanted;

FIG. 15 shows a further exemplary embodiment of the device according to embodiments of the invention, the device again being equipped for e.g. drug delivery to the non-accessible side of a hard tissue layer through which the device is implanted;

FIG. 16 shows an exemplary embodiment of a device part according to embodiments of the invention, the device part constituting an access port reaching from the accessible side to the non-accessible side of a hard tissue layer (e.g. to inside of cranial bone or to medullary cavity of tubular bone).

DETAILED DESCRIPTION OF THE PREFERRED EMBODIMENTS OF THE INVENTION

Figure 1:
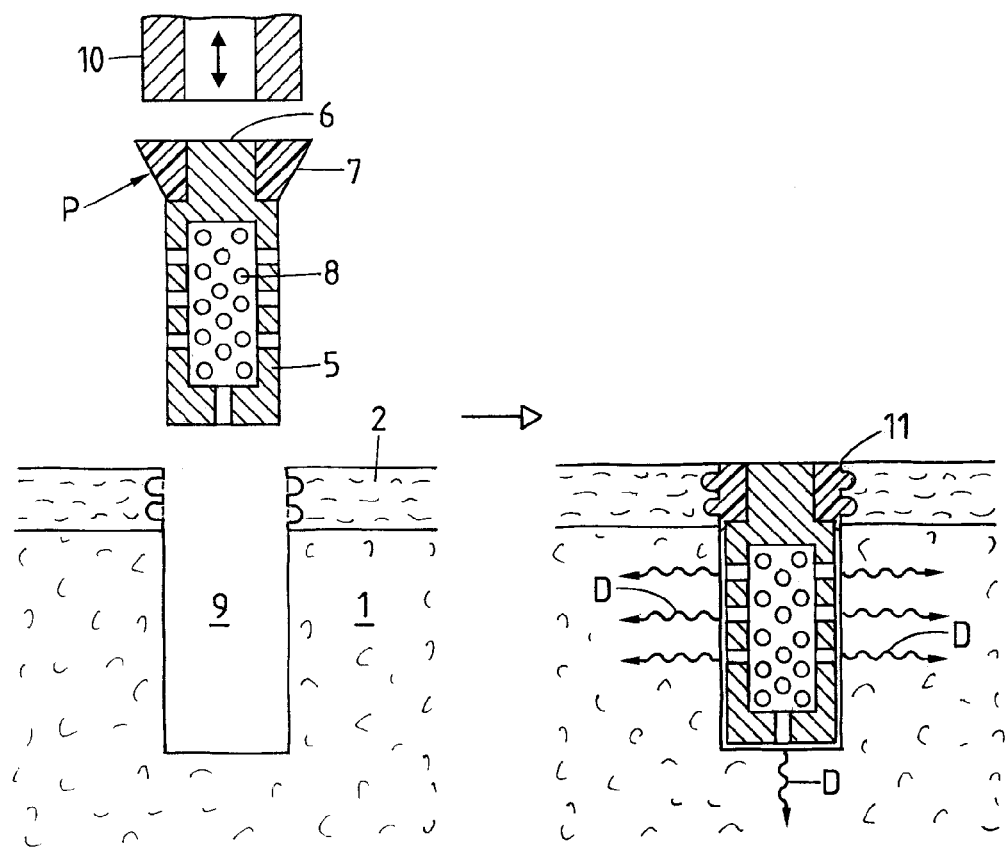
FIGS. 1 and 2 show an exemplary device according to embodiments of the invention and an exemplary application (intra-osseous drug delivery) thereof, the devices serving for fixed implantation and being equipped for e.g. drug delivery to the non-accessible side of a hard tissue layer through which the device is implanted.

FIG. 1 shows an exemplified embodiment of an implantable drug delivery device according to the invention. The device is suitable for drug delivery D to tissue situated on a non-accessible side of a hard tissue layer (i.e. side which is accessible only through the hard tissue layer), in the exemplary case as illustrated drug delivery to cancellous bone tissue 1 beneath a cortical bone layer 2 (intra-osseous drug delivery). For implantation of the device, the cortical bone layer 2 is perforated from its accessible side opposite the cancellous bone tissue. FIG. 1 shows the device, axially sectioned, ready for implantation (left hand side) and after implantation (right hand side).

The device comprises a plug portion P and a container 3 which e.g. extends distally of the plug portion P and is substantially cylindrical. The container 3 has a distal wall portion 5 which is perforated, fenestrated, or otherwise suitably permeable (distal portion of lateral wall and/or distal wall of a cylindrical container) and a proximal wall portion 6 which is non-permeable (proximal wall and/or proximal part of lateral wall of a cylindrical container). In the illustrated case, the non-permeable proximal wall portion is constituted by the plug portion P. The ring 7 of the material having thermoplastic properties is arranged between permeable and non-permeable wall portion, in the illustrated case around the plug portion P or the proximal region of the cylindrical container 3 respectively and preferably has a slightly larger diameter than the lateral container wall. The container 3 is e.g. made of a metal, a ceramic material or of a polymer material which may or may not have thermoplastic properties, in particular, it may be made of the same material having thermoplastic properties as the ring 7. An axial length of the device is preferably greater than the thickness of the hard tissue layer (e.g. cortical bone layer 2) through which the device is to be implanted. The drug or a combination of drug and drug carrier (e.g. drug integrated in drug carrier particles 8, in drug carrier tablets or in a drug carrier gel) is contained within the container 3.

For implanting the device of FIG. 1, an opening 9 is provided in the desired location of the bone, wherein a proximal cross section of the device or of the ring 7 respectively is slightly larger than the cross section of the mouth of the opening, and wherein the opening reaches into the cancellous bone tissue 1 to a depth which is sufficient for accommodating the container portion having permeable walls. The device is positioned in the opening 9 with the ring 7 sitting in the opening or on the mouth of the opening. Then energy is transferred at least to the ring 7 and the device is at the same time pressed into the opening 9. For this purpose, e.g. a sonotrode 10 coupled to an active ultrasonic device is applied to the positioned device and pressed against the latter, wherein the sonotrode e.g. has a cross section adapted to the ring 7 as illustrated. The sonotrode 10 may also be equipped with means for holding the device and be used also for positioning the device for implantation (not shown).

Vibration and pressing cause friction between the bone wall of the mouth region of the opening 9 and the ring 7 to generate heat for liquefaction of the ring material, which at the same time is brought into intimate contact with this bone wall. Simultaneously, the device is moved deeper into the opening. The vibration is stopped advantageously when the proximal face of the device is about flush with the bone surface, although, on stopping the vibration, the proximal face of the device may also be situated above or below the bone surface as long as the achieved anchorage of the ring 7 in the cortical bone layer 2 and advantageously in a transition region between cortical and cancellous bone tissue is sufficient to form a complete sealing ring 11.

As shown on the right hand side of FIG. 1, on re-solidification of the ring material, this material forms a sealing connection (sealing ring 11) with the bone tissue and, if this bone tissue comprises corresponding cavities or pores, a positive fit connection with the bone tissue. For achieving such positive fit connection in hard tissue having only little natural porosity such as cortical bone, e.g. a thread or other suitable surface structure may be provided in the mouth region of the opening 9. A positive fit connection can be achieved also with a ring 7 being dimensioned for reaching deep enough into the opening 9 such that ring material is liquefied not only in the depth of the cortical bone layer but also in the depth of a transition zone between cortical and cancellous bone, where the bone tissue comprises enough porosity for achieving a positive fit connection.

In addition to extending on the distal side of the plug portion P, the container may also extend through the plug portion and on the proximal side of the plug portion (similar to the device shown in FIG. 3), but having in the named regions no permeable walls, wherein after implantation the proximal container part will protrude from the cortical bone on its accessible side.

Instead of using vibrational energy for the implantation process as illustrated in FIG. 1 it is possible also to use a pressing tool comprising a light guide connected to a laser light source and suitable for transmitting laser light into or through the ring 7 to be absorbed in the ring or beneath the ring for providing the thermal energy necessary for liquefaction of the ring material. Alternatively, the ring 7 or device portions adjacent to the ring may be equipped for resistive or inductive heating and the pressing tool is equipped for transmitting the necessary electric or electromagnetic energy.

As mentioned above, the drug (as an example of the material or signal delivery or acquisition portion of the device) is arranged inside the container 3. The configuration in which the drug is present and the container perforation, fenestration, or other suitable permeability are adapted to each other to achieve a desired delivery rate and/or delivery profile. If the permeable distal wall portion is designed such that it constitutes no substantial hindrance or a baffle only for the passage of the drug, a desired delivery rate and/or profile is to be achieved by providing inside the container a suitable combination of drug and drug carrier (further example of the material or signal delivery or acquisition portion of the device), i.e. a complete drug delivery system, for which the implantable container figures as means for fixed implantation only and influences the characteristics of the delivery process to a very small degree at the most. Such a drug delivery system may comprise one or a plurality of per se known drug carriers such as a gel, liposomes, nanoparticles, microspheres, beads or tablets, in which the drug is integrated, or containments, capsules or porous bodies of e.g. a polymer, ceramic or metallic material, in which the drug is contained. The drug is released from the delivery system due to bioresorption, dissolution or disintegration of the carrier material or due to diffusion or osmosis.

The above discussed permeability of container wall portions is to be adapted to the use of the device, which means that in a device for material delivery or acquisition such permeability is to enable passage of the application specific materials, in a device for signal delivery or acquisition the permeability is to enable passage of the specific signals.

On the other hand, it is possible also that the container 3 is equipped to play a more direct role in the drug delivery process. Its permeable distal wall portion 5 may e.g. be made at least partly of a bioresorbable, soluble or disintegrating material which becomes permeable for the drug only after a specified degree of resorption, dissolution or disintegration (delayed delivery). Furthermore, the permeability of the wall 5 may be so restricted as to limit the drug delivery rate as desired (slow delivery) without the necessity of further limiting means such as the above named drug carriers. Furthermore, a fenestration of the permeable wall section may be closed by a semipermeable membrane through which an osmotic pump driving the delivery system is fed.

Figure 2:
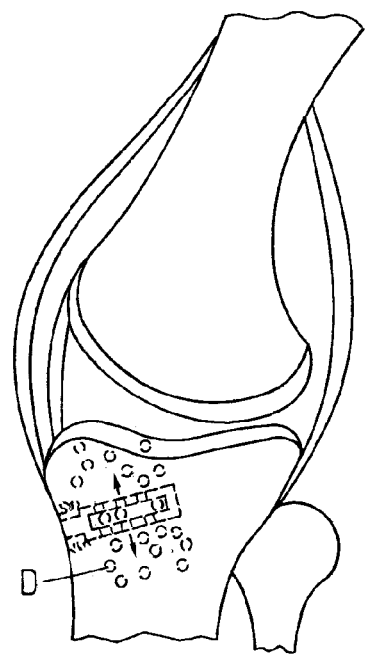

FIG. 2 illustrates an exemplary application of the intraosseous drug delivery D with the aid of a device according to FIG. 1. The device as illustrated is implanted on a lateral side of the tibial condyle just below the capsule of the knee joint, the intra-osseous drug delivery D (illustrated as arrows and dark dots spreading in the bone tissue away from the drug delivery device) being aimed at bone tissue near the articular surface of the tibia.

Local intra-osseous drug delivery with the aid of a drug delivery device, as illustrated in FIG. 1 or 2, may e.g. serve for delivery into the bone tissue of an antibiotic or anti-inflammatory drug, of a drug furthering bone regeneration, or a drug for battling bone cancer. Exemplary applications are: local prophylaxis and supportive treatment of chronic or acute osteomyelitis in a human patient (e.g. after open fracture or bone surgery) by local slow-release intra-osseous delivery of an antibiotic formulation (e.g. gentamicin, vancomycin, amoxicillin, cephalosporine); prophylaxis or treatment of infections subsequent to endoprosthesis surgery (primary or redo surgery) by local slow-release intra-osseous delivery of an antibiotic (e.g. gentamicin or vancomycin) near the part of the endoprothesis which is embedded in bone tissue; therapy or prophylaxis of osteomyelitis, septic phycitis or bone fracture infection in animal patients by local slow-release intra-osseous delivery of an antibiotic (e.g. gentamicin, amikacin, cephalosporine); prophylactic and therapeutic treatment (acute or secondary treatment) of complex and difficult to heal fractures, pseudoarthritis and non-union fractures by local intra-osseous delivery of bone growth factor (e.g. BMP-2 or BMP-7) near the fracture site; support of spinal fusion by controlled local intra-osseous delivery of a bone growth factor (e.g. BMP-2 or BMP-7) near or at the fusion site; support of tendon or ligament repair by local delivery of a bone growth factor (e.g. BMP-2 or BMP-7) near the tendon/bone or ligament/bone interface; palliative local treatment of inoperable symptomatic or unstable bone metastases or adjuvant therapy after surgical removal (e.g. grade IV breast and prostate cancer with one or more symptomatic bone metastasis) by slow-release intra-osseous delivery of an anticancer drug (e.g. methotrexate or cisplatin) in or proximal to the metastatic lesion; bone regeneration after surgical removal of symptomatic or unstable bone metastases by slow-release intra-osseous delivery of a drug that stimulates bone formation and/or inhibits bone destruction (e.g. bone growth factors, bisphosphonates); treatment of avascular bone necrosis; treatment against local pain.

In all above listed applications, the drug delivery device according to the invention is preferably implanted through a cortical bone layer and equipped for delivery in the cancellous bone therewith restricting delivery to the bone tissue. However it is possible also to implant a similar device through a surgically made bone surface without a cortical layer and therewith without a sealing function. Such implantation is e.g. possible in the applications of prophylaxis of infections subsequent to endoprosthesis surgery (primary or redo surgery) by local slow-release delivery of an antibiotic (e.g. gentamicin or vancomycin) near the endoprosthesis surface in contact with bone tissue.

Instead of for local drug delivery, the device and method according to FIGS. 1 and 2 are also suitable for systemic delivery, wherein the drug is delivered to the cancellous bone tissue and the excellent blood supply within this cancellous bone tissue is exploited. Instead of intra-osseous drug delivery, device and method as illustrated in FIGS. 1 and 2 may also be used for extra-osseous delivery on a non-accessible side of a hard tissue (e.g. bone) layer, if the device is implanted through the hard tissue layer and reaching into a body cavity or into other tissue on the non-accessible side of the hard tissue layer. Applications for such use are e.g. drug delivery through the skull bone into the intracranial space or the cerebrospinal fluid respectively, delivery through a long bone into the medullary cavity or the bone marrow respectively, or delivery through facial bone into a sinus cavity.

Figure 3:
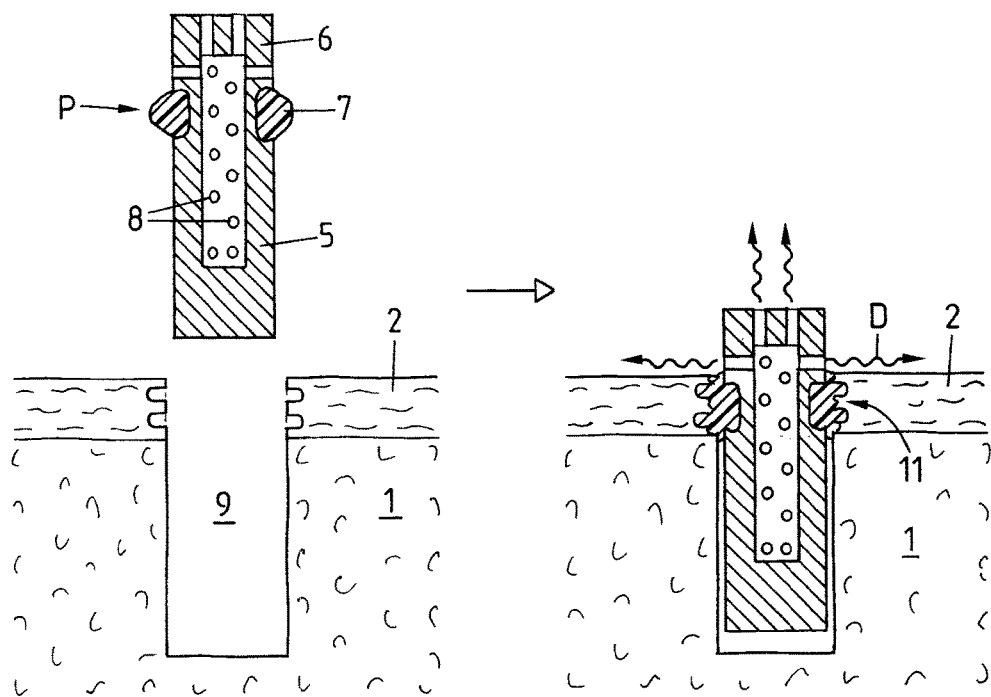
FIGS. 3 and 4 show exemplary devices according to embodiments of the invention and an exemplary application (intra-articular drug delivery) thereof, the devices serving for fixed implantation and being equipped for e.g. drug delivery to the accessible side of a hard tissue layer through which the device is implanted.

FIG. 3 illustrates a further embodiment of device and method according to the invention, which however has many similarities with the embodiment according to FIG. 1. Same items are denominated with same reference numerals as in FIG. 1. Other than the device according to FIG. 1, the device according to FIG. 3 is designed for drug delivery D on the accessible side of the hard tissue layer (cortical bone layer 2) through which it is implanted (extra-osseous drug delivery on the accessible side of a hard tissue layer, e.g. drug delivery into a cavity or tissue adjacent the cortical bone layer, e.g. into a joint capsule). For this reason the distal wall portion 5 of the container 3 is non-permeable and the proximal wall portion 6 is permeable and may or may not extend proximally from the plug portion P or the ring 7 of the thermoplastic material, which as in FIG. 1 separates the two wall portions 5 and 6. This ring 7 is e.g. arranged in an undercut groove running around the device, wherein the ring protrudes from the groove such increasing the diameter of the container slightly (plug portion P). It is obvious that such a ring does not need to be complete to start with, but may comprise circumferential gaps as long as it comprises enough of the thermoplastic material to, in the liquefied state, fill the whole groove and constitute a sufficient sealing ring 11.

As shown on the right hand side of FIG. 3, the device is not implanted to be flush with the bone surface, but in the implanted state protrudes from the opening 9. Alternatively the device may be implanted to be flush with the bone surface, in which case, the ring 7 of thermoplastic material would be positioned at the proximal device end (as illustrated in FIG. 1) and the permeable proximal wall portion 6 would be restricted to the proximal device face. As discussed in connection with FIG. 1, also the device according to FIG. 3 may be made of at least two different materials or it may consist fully of the material having thermoplastic properties, wherein the ring 7 would be an integral part of the whole device and would preferably protrude slightly over the lateral container wall.

Figure 4:
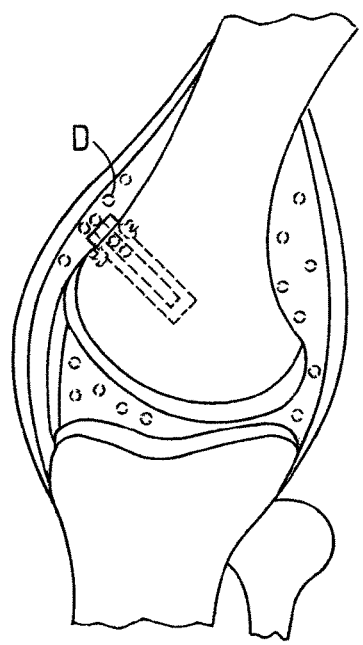

FIG. 4 shows in the same manner as FIG. 2 an exemplary application of the device according to FIG. 3, which is implanted on a lateral side of a femoral condyle within the capsule of a knee joint, the drug delivery D (illustrated with dark dots) being aimed at the synovial liquid contained in the capsule or at tissue (e.g. cartilage) being in contact with the synovial liquid. Exemplary applications of such drug delivery concern the local supportive treatment or prophylaxis of acute, sub-acute or chronic joint infections (e.g. septic arthritis with or without adjacent bone and soft tissue involvement) in an animal patient by slow-release intra-articular delivery of an antibiotic (e.g. gentamicin, amikacin, cephalosporin) into the synovial liquid of the affected joint or long-term therapy of inflammatory or degenerative joint diseases by long-term delivery of an anti-inflammatory drug (e.g. cortisone) into the synovial liquid of the affected joint. In the same manner as above described for implantation inside a joint capsule, the device may be implanted in other bones, the drug delivery being aimed at a cavity or liquid or at a tissue other than bone tissue on the accessible side of the bone.

FIG. 5 shows a drug delivery device (implanted configuration) which is very similar to the drug delivery device according to FIG. 1. Other than shown in FIG. 1 the ring 7 of the material having thermoplastic properties is not arranged around a plug portion to be introduced into the opening 9, but on the hard tissue facing surface of a cover portion C for the ring material to be anchored in the hard tissue surface around the mouth of the opening 9. Therefore, the ring 7 has a diameter larger than the diameter of the opening 9. The device comprises again a container 3 with a distal and a proximal wall portion (5, 6), wherein the proximal wall portion 6 is constituted by the cover portion C and is non-permeable and wherein the distal wall portion 5 comprises a perforation, fenestration or other suitable permeability and extends distally from the cover portion C. FIG. 5 shows the implanted device, the ring 7 being sealingly anchored in the outer surface of the cortical bone layer 2 and there constituting the sealing ring 11. For achieving a good seal and a positive fit connection between the bone tissue and the ring 7 it may be advantageous to roughen the named bone surface before implanting the device.

Of course it is possible to dimension and/or equip the container area adjoining the cover portion C of the device of FIG. 5 as a plug portion, i.e. comprising a further ring of a material having thermoplastic properties, and to anchor not only the ring of the cover portion C in the bone surface but also the ring of the plug portion in the wall of the opening, wherein it is a condition that the anchorage of both rings together form a complete sealing ring 11, but wherein it is not a condition that each ring by itself forms a complete sealing ring.

FIG. 6 shows a further drug delivery device which is similar to the drug delivery device according to FIG. 5 but, when implanted through a hard tissue (e.g. bone) layer, serves for (extra-osseous) drug delivery on the accessible side of the hard tissue layer, as described above in connection with FIGS. 3 and 4 (e.g. intra-articular drug delivery, i.e. drug delivery into the synovial fluid of a synovial joint). The device according to FIG. 6 differs form the device according to FIG. 5 in that it is the proximal wall portion 6 (cover portion C) which is permeable, while the distal wall portion 5 is non-permeable.

If the cover portion of the device as shown in FIG. 6 is fully made of the material having thermoplastic properties it may also be fixed to the bone surface around the opening 9 in an orientation opposite to the illustrated one, i.e. with the container extending in a proximal direction, i.e. away from the bone surface. If implanted in such an orientation, the same device is capable of intra-osseous drug delivery, if the depth of the opening 9 is at least as great as the thickness of the cortical bone layer.

In both devices as shown in FIGS. 5 and 6, the container may extend into the cover portion C or protrude proximally from the cover portion. Material, functions and applications of the devices as shown in FIGS. 5 and 6 are substantially the same as the ones described in connection with the devices shown in FIGS. 1 to 4.

The drug delivery devices and implantation methods as illustrated by FIGS. 1 to 6 may be varied without departing from the invention e.g. in the following manner:

Instead of substantially cylindrical, the device may be e.g. conical or stepped and fit into a tapering or stepped hard tissue opening. Also the axial length of the device may be larger, the same or smaller than its diameter and the device and/or the ring of the thermoplastic material may have a cross section of any form, in particular a non-circular cross section. The great variability of the form of the device and therewith of the form of the container 3 allows adaptation to a large number of drug/carrier combinations which are available on the market for administration other than with the aid of a device according to the invention.

The container of the device may comprise a closable proximal opening which is suitable for the drug or drug/carrier combination to be filled into the container, when the device or part thereof is positioned for implantation or is implanted in the hard tissue already. The opening is then closed by e.g. ultrasonically welding a closure element into it, which closure element may at the same time constitute the cover or plug portion of the device and is anchored in the hard tissue for producing the sealing ring simultaneously with being welded to a lateral wall portion of the container for closing the container.

A proximal opening of the container may be capable of being closed, re-opened and re-closed (e.g. a septum to be penetrated with a hollow needle). The drug or drug/carrier composition is filled into the implanted device through the opening and the opening is then closed or closes itself. For re-filling (in the implanted configuration of the device), the opening is re-opened and then re-closed.

A permeable distal or proximal wall portion of the container may be flexible (e.g. consisting of a textile material) and attached to a non flexible plug or cover portion.

The device comprises instead of a container, a drug/carrier combination which is capable of taking over the function of at least the permeable distal or proximal wall portion and which is attached to the plug or cover portion of the device. Such drug/carrier combinations are e.g. pieces of a bioresorbable material or a material with an open porosity.

Instead of or in addition to a drug or drug/carrier combination, the container may contain other material or signal delivery or acquisition portions such as e.g. an electronic element and serve, possibly in cooperation with further device parts, for signal delivery or acquisition within the body in which it is implanted. Depending on the signals to be emitted or received and depending on the material of the container walls it may in such a case not be necessary for the container walls to comprise perforations. The electronic element is e.g. an RFID-chip. It is possible also to attach the electronic or other signal emitting or receiving element directly to the plug or cover portion without the use of a container.

Instead of or in addition to a drug or drug/carrier combination, the container may comprise a radiation source for alpha- or beta-radiation, wherein wall portions not to be permeable for the radiation contain e.g. barium sulfate or tantalum.

Instead or in addition to a drug of drug/carrier combination, the container contains cells in a suitable suspension or matrix, which cells are capable of forming a locally desired tissue (stem cells or further differentiated cells such as e.g. osteoblasts) or are engineered for production of proteins suitable for local therapeutic or otherwise beneficiary purposes (e.g. growth factor or bone morphogenic factor).

The device is equipped for drug delivery on the non-accessible side of the hard tissue layer through which it is implanted, in particular for intra-osseous delivery and is not implanted in a hard tissue opening which is specifically made for the implantation and correspondingly adapted to the device, but it is implanted in an opening in the hard tissue layer of an other origin (e.g.

surgery, accidental fraction). For adapting the device to the opening it is possible to choose a corresponding device or to implant a plurality of devices such that the sealing function of each device is achieved by a sealing ring which sealingly contacts not only the hard tissue but also one or a plurality of other similar devices. The same applies for devices being implanted in openings adjacent to an endoprosthesis serving a completely different purpose from the purpose of the inventive device.

The above listed exemplary variations of the devices and methods as illustrated in FIGS. 1 to 6 are at least partly applicable also for the devices and methods as illustrated in the following Figs., wherein one skilled in the art will easily find possible combinations and possibly necessary adaptations.

Figure 9:
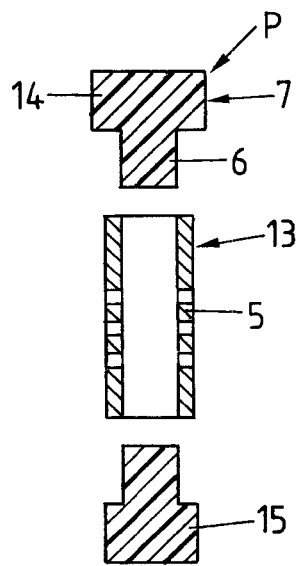

FIGS. 7 to 9 show further exemplary forms of the device according to the invention as shown in FIGS. 1 and 2, the devices being applicable for drug delivery on the non-accessible side of the hard tissue layer through which they are implanted (e.g. intra-osseous drug delivery) and comprise substantially cylindrical containers 3 extending distally from a plug portion P and comprising a permeable distal wall portion 5.

According to FIGS. 7 and 8, the device comprises a substantially cylindrical container 3 with a fenestrated distal wall portion 5 and a plug portion P constituting the ring of the thermoplastic material and the non-permeable proximal wall portion (not visible) of the container. The drug or combination of drug and drug carrier (not shown) is positioned in the container 3 either from its distal or proximal end wherein an entry port at the proximal end is to be tightly closed with a corresponding closure element (not shown) and an entry port at the distal end is to be sufficiently closed with suitable means (e.g. cross pin 12 of FIG. 3) for preventing the drug or drug delivery system respectively from departing from the container for at least as long as the device is not implanted yet. For application in the human locomotor system, devices as shown in FIGS. 7 and 8 have a length of e.g. between 20 and 30 mm, outer diameters of e.g. 3 to 10 mm, and inner diameters of 1 to 8 mm. The ring 7 has an outer diameter which is e.g. 1 mm larger than the outer diameter of the distal container region and an axial length of at least in the order of 5 mm (for intra-osseous drug delivery or implantation through a cortical bone layer respectively). For applications in smaller and/or thinner human bones (e.g. neurosurgical and maxillofacial applications) and in small animals the devices are correspondingly smaller, for applications in larger animals correspondingly larger (equine applications: device length up to e.g. 150 mm).

Plug portion P and container 3 are e.g. made as one piece and consist of the material having thermoplastic properties, e.g. of polylactide. If the material is bioresorbable, as is the case for polylactide, its resorbability is to be adapted to the drug delivery process such that resorption at least in the region of the ring 7 or the sealing ring 11 respectively does not start or does not relevantly impair the sealing function before delivery of the drug is substantially complete.

FIG. 9 is an exploded axial section of a further exemplary form of the device according to the invention as shown in FIG. 1. The device comprises a tube element 13 having a perforated, fenestrated or otherwise suitably permeable wall and constituting together with a distal closure element 15 the permeable distal wall portion 5 of a container. The device further comprises a proximal closure element 14, which consists of the material having thermoplastic properties, has a slightly larger cross section than the tube element 13, and constitutes the plug or cover portion P or C with the ring 7 of the material having thermoplastic properties and the non-permeable proximal wall portion 6. Advantageously, both closure elements consist of the material having thermoplastic properties and the tube element 13 is e.g. a metal tube. The device as shown in FIG. 9 is advantageously assembled and loaded with the drug or drug/carrier combination or other element for material or signal delivery or acquisition and is then implanted as described further above for the device of FIG. 1. Depending on the depth of the opening provided in the hard tissue for the device, on the mechanical properties of the hard tissue on the bottom of this opening, and on the form of the distal face of the device, anchorage in the hard tissue in the region of the distal closure element is possible similar to the anchoring in the mouth region of the opening.

Instead of the tube element 13 comprising the fenestration perforation or other permeability, the tube element 13 may have a non-permeable wall and the distal closure element 15 may be correspondingly permeable. If, of the two closure elements, one is permeable and the other one is non-permeable and both closure element have substantially the same form, it is possible to use the same device for applications as described in connection with FIG. 2 and in connection with FIG. 4, wherein the device, depending on the application, is implanted with the permeable closure element either leading or trailing.

Figure 10:
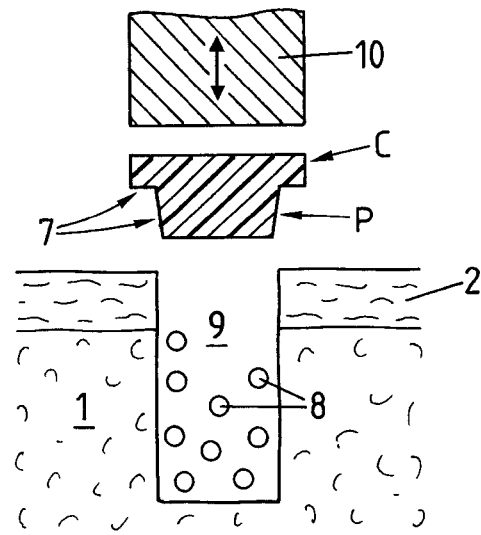

FIG. 10 shows a further exemplary embodiment of a drug delivery device according to the invention which device is equipped for delivering a drug to the non-accessible side of a hard tissue layer, e.g. to cancellous bone 1 beneath a cortical bone layer 2. The device comprises a plug portion P and/or a cover portion C adapted in the above described manner to the opening 9 which is provided in the bone tissue. The plug and/or cover portion substantially constitute the non-permeable proximal wall portion and the ring 7 of the material having thermoplastic properties as discussed in connection with FIGS. 1 to 9, wherein the function of the permeable distal wall portion is taken over by the walls of the opening 9 in the tissue on the non-accessible side of the penetrated hard tissue layer (in particular cancellous bone tissue 1 on the non-accessible side of the cortical bone layer 2). The drug or drug/carrier combination or other material to be delivered to the cancellous bone tissue (e.g. bioresorbable carrier particles 8 or tablets in which a drug is integrated, a saline solution in which e.g. a growth factor is suspended or dissolved or a suspension or suitable matrix comprising cells capable of producing e.g. extracellular bone matrix material or factors furthering bone growth) is introduced in the opening 9, the plug portion P and/or cover portion C is then sealingly anchored in the wall of the opening 9 and/or in the bone surface around the mouth of the opening substantially as described in connection with the drug delivery devices as illustrated in FIGS. 1 to 9.

Figure 11:
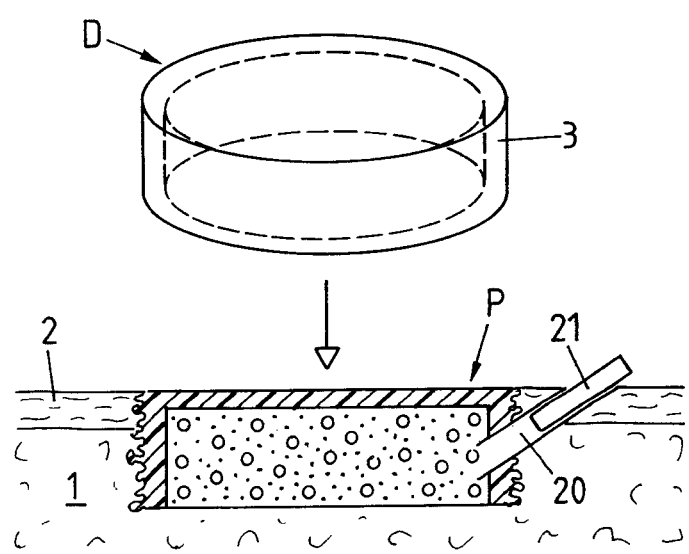

FIG. 11 shows a drug delivery device having similar features as the device illustrated by FIG. 10. The device comprises a plug portion P and extending distally from the latter a container having only lateral walls which may be perforated, fenestrated or otherwise permeable or not the absent distal wall constituting the only or an additional fenestration. The plug portion constitutes the non-permeable proximal wall portion of the container. The device is implanted e.g. to cover a bone defect, wherein anchorage in the walls of the opening may extend over the whole axial length of the device (for non-permeable lateral wall or between fenestrations). As the container 3 of the device according to FIG. 11 has no distal wall, it is advantageous to introduce the drug or drug/carrier combination after implantation, e.g. through a lateral channel 20 which is drilled after implantation of the device and which, after filling the container 3, is closed with e.g. a bone plug 21 or a plug of a material having thermoplastic properties being "welded" into the channel 20 using ultrasonic vibration energy.

FIGS. 12 and 13 show again drug delivery devices for drug delivery on the non accessible side of a hard tissue layer, e.g. to cancellous bone tissue 1 beneath a cortical bone layer 2 or to bone marrow in a long bone, wherein the drug is released at a distal device end only. The devices comprise again a container 3, wherein the lateral container wall is not permeable and therefore the whole axial length of the device may constitute the plug portion P or in other words the axial length of the ring 7 of the material having thermoplastic properties and of the sealing ring 11 may extend over substantially the whole axial length of the device.

Figure 12:
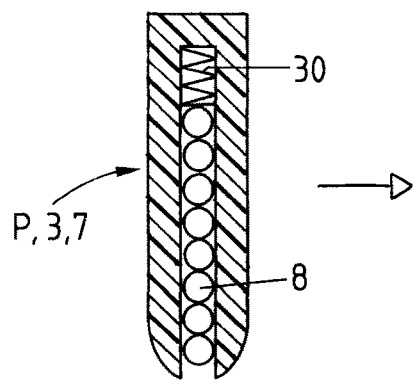
Figure 12:
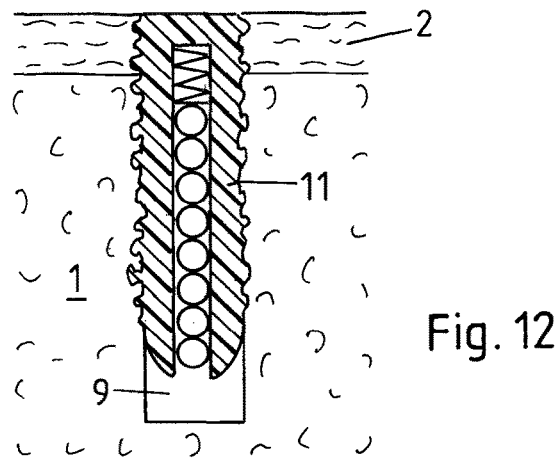

In the embodiment according to FIG. 12, the inner space of the container 3 has a diameter adapted to the diameter of biodegradeable drug carrier beads 8 or tablets being arranged in this space in a row or chain, which is biased against a slightly narrower distal exit port e.g. by a spring 30. As soon as the first carrier bead nearest to the exit port is resorbed sufficiently to be capable to pass the exit port, the next second carrier bead which beforehand was shielded from the resorbing media by the first carrier bead is pushed to the exit port and subjected to resorption.

Figure 13:
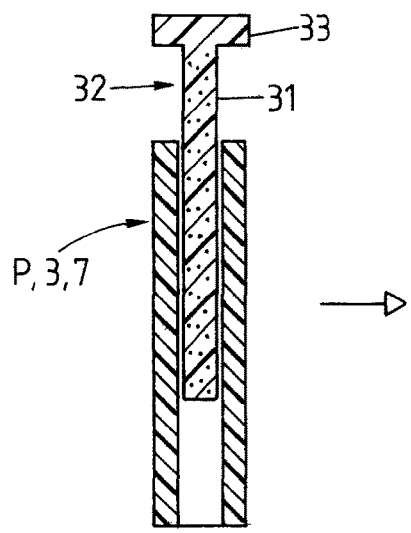
Figure 13:
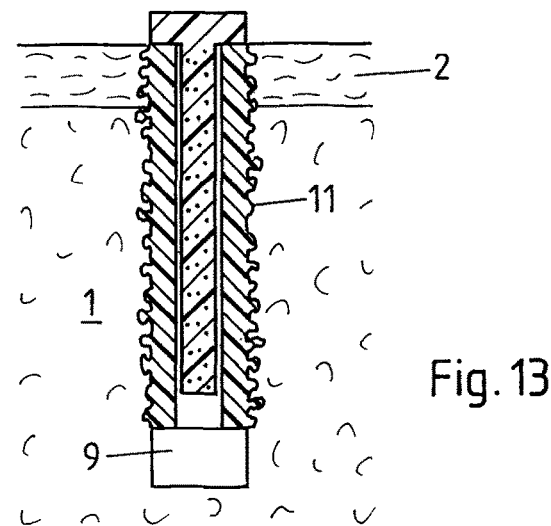

In the embodiment according to FIG. 13 the drug is contained in the shaft 31 of a nail-shaped drug carrier 32. The head 33 of the nail-shaped drug carrier does not contain the drug and fits as a closure element onto the tube shaped container 3 or plug portion P respectively. The drug nail 32 is introduced into the plug portion P before or after implantation of the latter and the head 33 is advantageously welded (e.g. with the aid of ultrasonic vibration energy) to the proximal face of the plug portion P. It is possible also to dimension and equip the head 33 as a plug portion and/or closure portion C to be anchored in the wall of opening 9 and/or in the hard tissue surface around the mouth of opening 9. In such a case, the tube-shaped container 3 is positioned in the hard tissue opening, the drug nail 32 being introduced in the latter before or after positioning of the container and then the head is welded to the container and at the same time anchored in the hard tissue. Drug delivery is effected by biodegradation or dissolution of the shaft of the carrier nail or by diffusion out of this shaft.

Figure 14:
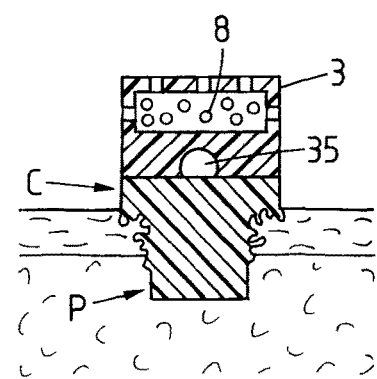
FIG. 14 shows a further exemplary embodiment of the device according to embodiments of the invention, the device again being equipped for e.g. drug delivery to the accessible side of a hard tissue layer through which the device is implanted.

FIG. 14 shows a further drug delivery device according to the invention which device is suitable for drug delivery to the accessible side of the hard tissue layer through which the device is implanted. The device comprises a perforated or fenestrated drug container 3 or drug/carrier tablet and a non-permeable plug portion P (possibly combined with a cover portion C), wherein the drug container is releaseably attached to a proximal side of the plug or cover portion, e.g. with the aid of a snap connection 35. When attached, the container is situated on or above the hard tissue surface of the accessible side of the hard tissue layer. The plug portion is preferably implanted in the hard tissue opening before the container is attached to it.

FIG. 15 illustrates a further embodiment of a drug delivery device according to the invention and a method for implanting the device. The device is equipped for drug delivery on the non-accessible side of a hard tissue layer, e.g. for intra-osseous drug delivery through a cortical bone layer. However, if adapted as described further above for other embodiments of the device according to the invention, the device may also serve for drug delivery on the accessible side of the hard tissue layer.

The device comprises in a similar way as the device according to FIG. 9, a substantially cylindrical container constituted by a tube element 13 with perforated or fenestrated walls 5 and a proximal closure element 14 which constitutes the plug portion P possibly combined with a cover portion C, i.e. comprises a ring 7 of a material having thermoplastic properties around the plug portion P and possibly also on the hard tissue facing surface of the cover portion C. The tube element 13 has an open proximal end and an open or closed distal end, wherein the proximal closure element 14 fits into the proximal open end and the tube perforation continues right to this proximal end. The device may further comprise a distal closure element 15, which comprises a material having thermoplastic properties being the same or different from the material of the proximal closure element 14. The closure element 15 is positioned at the bottom of the tube element 13. It serves for anchoring the device in the bottom of a hard tissue opening 9 for which purpose the distal end of the tube element 13 needs to comprise a perforated or fenestrated wall. The distal closure element may further serve for closing the distal end of the tube element 13 and/or for strengthening cancellous bone tissue in the area of the distal device end.

FIG. 15 shows three successive phases (a) to (c) of the implantation of the drug delivery device as described above. In phase (a), the tube element 13 is positioned in the hard tissue opening 9, which is dimensioned such that, at least in the region of its mouth, the tube element 13 is closely surrounded by the wall of the opening. The distal end of the tube element 13 may or may not rest on the bottom of the opening 9 (the tube element 13 may freely hang in the opening, if it comprises a proximal flange supported on the hard tissue surface around the mouth of the opening). If applicable, the distal closure element 15 is positioned at the bottom of the tube element 13 and a primary sonotrode 10' is introduced into the tube element 13 for effecting the distal anchorage by pressing the distal closure element 15 against the bottom of the tube element 13 and transmitting vibration to it for at least partly liquefying the thermoplastic material of this closure element and pressing it through the perforations or fenestrations of the tube element to penetrate tissue surrounding the latter.

In phase (b) the distal anchorage is completed and the primary sonotrode 10' removed. The drug or drug delivery composition (e.g. drug containment 42) is introduced into the tube element 13. The proximal closure element 14 is positioned on or into the proximal end of the tube element 13 and a secondary sonotrode 10" is applied to it for effecting closure of the tube element 13 and simultaneously for sealingly anchoring the tube element 13 in the hard tissue wall of the opening 9 by liquefying the material of the circumferential surface of the plug portion P (ring 7) and pressing it through perforations or fenestrations of the tube element 13 to get in contact with the walls of the opening 9 in the region of its mouth. If applicable, further material having thermoplastic properties arranged on the cover portion C is also liquefied. The re-solidified material then constitutes the sealing ring 11 between the device and the wall of opening 9 and possibly the hard tissue surface around the mouth of opening 9.

When effecting the distal and proximal anchorage of the device as shown in FIG. 12 care is to be taken, that enough of the perforation or fenestration of the tube element 13 is kept free of the material having thermoplastic properties for enabling passage of the drug. These perforations or fenestrations or another suitable permeability of the container wall may in a manner as discussed already further above constitute a simple baffle for the drug passage, wherein the drug delivery is substantially controlled by the drug delivery system contained in the container, or they may play a more direct role in the control of the drug delivery.

The exemplary embodiment of a drug delivery device according to the invention as illustrated in FIG. 15 may be varied in the following manner:

The tube element 13 comprises a proximal flange, which is perforated or fenestrated and the proximal cover element 14 comprises a cover portion C whose ring 7 of the material having thermoplastic properties is anchored in the hard tissue surface through the flange perforations.

Anchorage of the tube element 13 may regard the complete perforation thereof, the proximal cover portion 14 being permeable, wherein in such a case the device serves for drug delivery to the accessible side of the hard tissue layer in which it is implanted.

FIG. 16 illustrates an implantable device part which serves as access port to a not directly accessible side of a hard tissue layer. Such access ports may e.g. serve for temporal or permanent access for an infusion cannula, a catheter, a sensor, an electrode, a light guide etc. wherein through the improvement according to the invention the natural sealing function of the hard tissue layer, which is impaired by implanting the access port, is fully mended. The access port as shown in FIG. 16 is implanted in a cranial bone for providing temporal or repeated access to the inside of the skull. In the same way access ports may be implanted through a tubular bone to provide access to the medullar cavity of the bone, through a cortical bone layer to provide access to cancellous bone tissue or a cyst or tumor beneath the cortical bone layer, through a facial bone to provide access to a sinus cavity or through a hard tissue opening which is closed by the device itself as e.g. a pocket caused by periodontitis between a tooth and the jaw bone The access port constitutes a part of a device for material or signal delivery or acquisition on the non-accessible side of the hard tissue layer.

FIG. 16 shows the access port before implantation (above) and in an implanted state (below). The access port comprises a plug portion P and/or a cover portion (not shown) as described above for drug delivery devices. The plug portion P comprises a circumferential ring 7 of the material having thermoplastic properties and a central septum element 50 of a material having elastic properties such that it is capable of being perforated with an element of small cross section (e.g. cannula, hollow needle) and to sealingly close the perforation around this element and again on removal of this element. Such materials which are e.g. elastomers on a silicone-basis, are well known from closures of containers allowing multiple access for filling syringes.

The access port is implanted in a through opening 9 provided in e.g. a cranial bone 51 with the aid e.g. of a sonotrode 10 and, in the implanted state, adjoins and is anchored in the walls of this opening 9 with a sealing ring 11 which guarantees together with the septum element 50 prevention of undesired passage through the cranial bone, wherein in the illustrated case prevention of passage of e.g. bacteria is particularly important.

Instead of comprising the septum element 50, the access port may comprise e.g. a cannula, a sensor, an electrode or other element reaching through the access port, which element is permanently installed in the access port and is temporally or permanently connected, connectable or cooperating with further device parts.

Applications of access ports as described above are e.g. providing access to a drug container located on the non-accessible side of the hard tissue layer for refilling, or emergency access to bone marrow through a wall of a tubular bone for administration of drugs to a patient suffering of peripheral vasculature collapse or in need of administration of a drug which is too aggressive for intravascular administration. The access port may be permanently connected to a drug reservoir or drug pump arranged e.g. subcoutaneously on the accessible side of the hard tissue layer in which the access port is implanted and being activated e.g. from outside the body or by the signal of a sensor which also passes through the access port. The access port may also be used for temporal passage of a light guide, possibly comprising a distal diffuser element, in order to deliver radiation energy (e.g. infrared light) to the inaccessible side of a hard tissue layer, e.g. for photodynamic therapy.

Instead of comprising the central septum element, the device according to FIG. 16 may comprise a central portion of a non-penetrable material or may consist completely of the material having thermoplastic properties. Such a device, which is implanted in the same manner as the access port according to FIG. 16, is part of a device serving for only one material delivery or acquisition step, wherein an opening through the hard tissue layer is provided, wherein material is delivered or removed from the accessible side of the hard tissue layer through the opening using a cannula or hollow needle and wherein the opening is then closed with the aid of the plug and/or cover portion which together with the cannula or hollow needle constitutes the full device for material delivery or acquisition.

Figure 17:
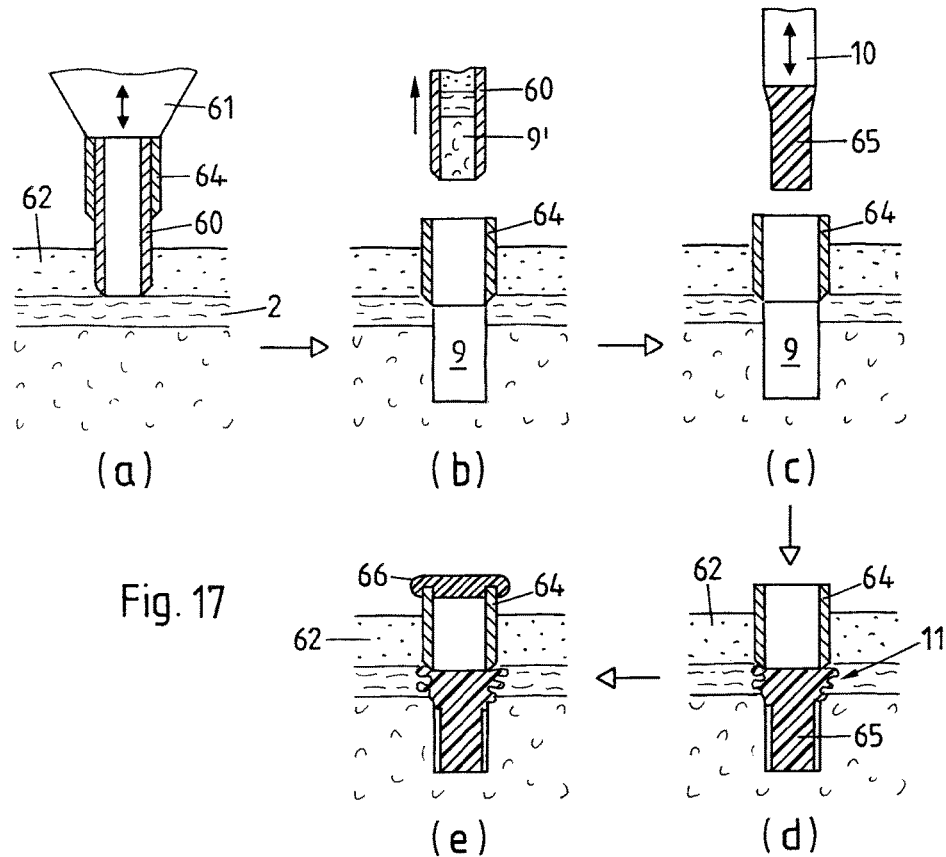
FIGS. 17 and 18 show successive phases of exemplary methods for percutaneous implantation of a device or device part according to embodiments of the invention.

FIG. 17 further illustrates percutaneous implantation of a device or device part as above described, in particular such implantation of a drug delivery device as described in connection with FIG. 1, 2, 7 or 8 or of an access port as e.g. described in connection with FIG. 16 and providing e.g. for permanent percutaneous access to the implanted device. FIG. 17 shows five successive phases (a) to (e) of the implantation process.

Phase (a) shows a hollow punching tool 60 being connected to an ultrasonic device 61 being positioned through the skin 62 on the accessible side of the hard tissue layer (e.g. cortical bone layer 2) in the position in which the device is to be implanted. The punching tool 60 carries in a proximal position a sleeve 64 of a smaller axial length. With the aid of the ultrasonic device 61 the tool 60 is forced through the skin 62 and through the hard tissue layer 2 to a desired depth and such that the sleeve 64 is positioned on the surface of the hard tissue layer 2 or slightly dug into it. Punching processes in which a punching tool 60 is driven by ultrasonic vibration energy are described in the publication US 2008/269649 whose disclosure is enclosed herein by reference.

Phase (b) shows the opening 9 being provided through the hard tissue layer 2, the sleeve 64 being positioned on the mouth of the opening and the punching tool 60 being removed together with the bone plug 9' from within the opening 9.

Phase (c) shows the implantable device 65 being held at the distal end of a sonotrode 10 and being introduced through the sleeve 64. Phase (d) shows the device 65 anchored in the hard tissue layer through the sealing ring 11 and percutaneously accessible through the sleeve 64 or the skin 62 respectively and phase (e) shows the sleeve 64 closed with a suitable cover 66.

Figure 18:
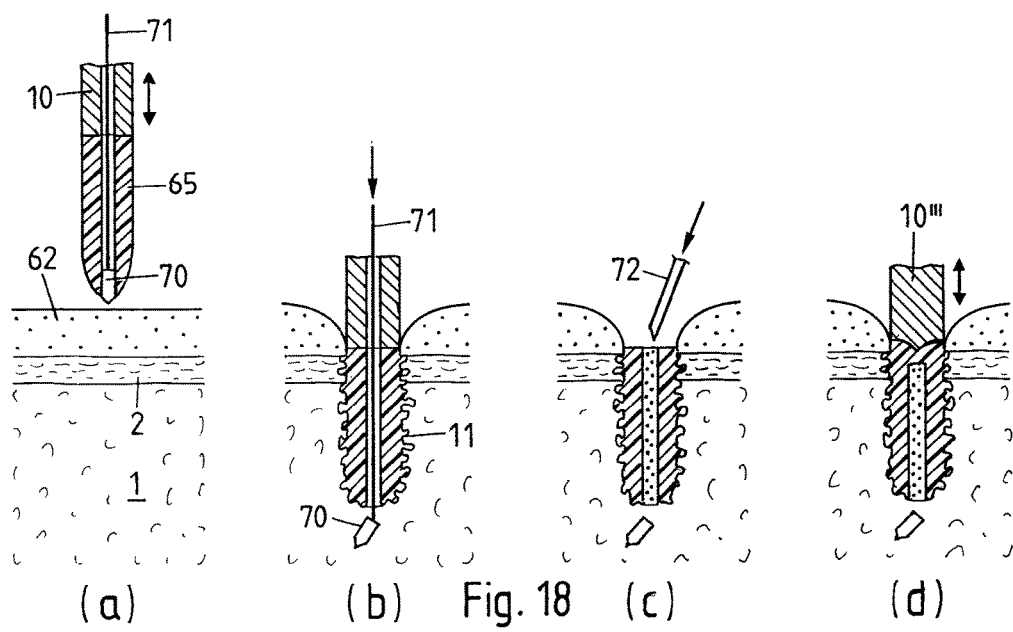

FIG. 18 illustrates a further embodiment of percutaneous implantation of a device 65 according to the invention, which device is a drug delivery device serving for drug delivery on the non accessible side of the hard tissue layer 2 through which the device 65 is implanted. The implantation is shown in four successive phases (a) to (d). The device is similar to the devices as shown in FIGS. 12 and 13 and comprises an axial channel whose distal mouth is initially blocked by a piercing element 70 which, by suitable means arranged in the channel, is prevented from being forced into the channel but not prevented from being forced out of the distal end of the channel. The substantially cylindrical device portion is preferably made of the material having thermoplastic properties, as illustrated, but may also comprise a metallic core. The piercing element 70 is e.g. a metallic element with a sharp distal end.

Phase (a) shows the device 65 being positioned for implantation and a sonotrode 10 applied to the proximal face of the device, wherein a K-wire 71 may be installed already to pass through the sonotrode 10 into the channel of the device 65. The device is forced through the skin 62 and through the hard tissue layer 2 (e.g. cortical bone layer) and simultaneously sealingly anchored (sealing ring 11) in the wall of the hard tissue layer 2 and possibly in tissue (e.g. cancellous bone tissue 1) located underneath the hard tissue layer by applying a pressing force and ultrasonic vibration energy to the sonotrode 10.

Phase (b) shows the device 65 implanted, the sonotrode 10 removed and the piercing element 70 being forced out of channel with the aid of the K-wire 71 which may be installed only after removal of the sonotrode.

Phase (c) shows the K-wire 71 removed and a cannula 72 introduced into the proximal mouth of the device channel for introducing the drug or drug/carrier combination into the channel. Phase (d) shows the cannula 72 removed and the device channel being closed by applying a further sonotrode 10''' to the proximal face of the device, wherein the further sonotrode has a distal face which is suitable for forcing liquefied material into the proximal mouth of the channel.

Figure 19:
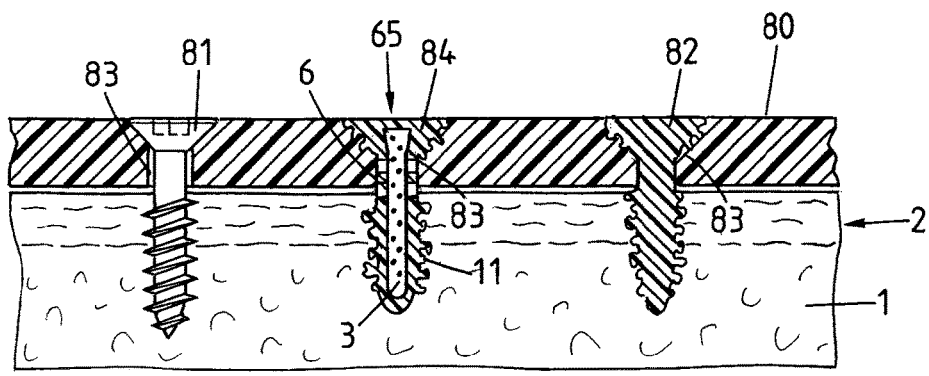
FIGS. 19 to 21 show further exemplary applications of the method according to the embodiments of invention

FIG. 19 shows a further exemplary application of the invention. This application regards prophylactic or therapeutic delivery of an e.g. antibiotic drug in a body region of e.g. osteosynthetic surgery, in particular such delivery between a bone surface and an osteosynthesis plate. Such plates are usually fixed to e.g. a fractured bone by bone screws, which are screwed into an opening provided in the bone or by pins comprising a thermoplastic material which are anchored in an opening provided in the bone through in situ liquefaction and bone tissue penetration followed by resolidification (caused e.g. by ultrasonic vibration applied to the pin), wherein the screw or pin is possibly secured to the plate simultaneously or with subsequent measures. The plate usually comprises a series of through openings, wherein the number of openings is usually larger than the necessary number of screws or pins, such that the surgeon can choose the most advantageous positions for the screws or pins. As shown in FIG. 19, at least one of such surplus openings is used for implanting the device according to the invention, wherein delivery of the drug is aimed at the gap between the plate and the bone surface underneath the plate.

FIG. 19 shows a section of an osteosynthesis plate 80 (or other plate such as e.g. an anterior cervical plate), which is e.g. made of a resorbable polymeric material, the plate being positioned against a surface of an e.g. fractured bone with the aid of a screw 81 or a thermoplastic pin 82, wherein both screw and pin reach through the plate 80 into at least the cortical bone 2 or further into the cancellous bone 1 for keeping plate and bone in a fixed local relationship. For both screw 81 and pin 82 the plate 80 comprises a through opening 83 and a corresponding opening is provided in the bone, wherein the pin 82 is anchored preferably in cortical and cancellous bone tissue, its head possibly being welded into the through opening 83 of the plate during the same application of vibrational energy. In a further through opening 83 and a corresponding opening in the bone, a device 65 according to the invention, e.g. a device similar to the device shown in FIG. 3, is implanted, the device being anchored as described further above at least in the cortical bone, but possibly also in the cancellous bone tissue where the thermoplastic material forms a sealing ring 11 on a plug portion which together sealingly close the opening in the bone. A head portion 84 of the device may further be welded into the through opening 83 of the plate 80 in a similar manner as above described for the thermoplastic pin 82.

The device 65 comprises a container 3 with a permeable proximal wall portion 6, having a suitable permeability proximally adjacent to the named anchorage 11 and e.g. reaching up to the head portion 84. Such an implanted device enables drug delivery to the space between the bone surface and an underside of the plate 80, which drug delivery is restricted to this space by the sealing ring 11 on the bone side and the weld between drug delivery device 65 and plate 80 on the other side.

If so desired, it is possible to design the proximal face of the device according to FIG. 19 as a permeable wall also, such that not only the gap between the plate and the bone surface, i.e. the plate surface facing the bone tissue, is treated with the drug to be delivered but also the opposite plate surface.

Figure 20:
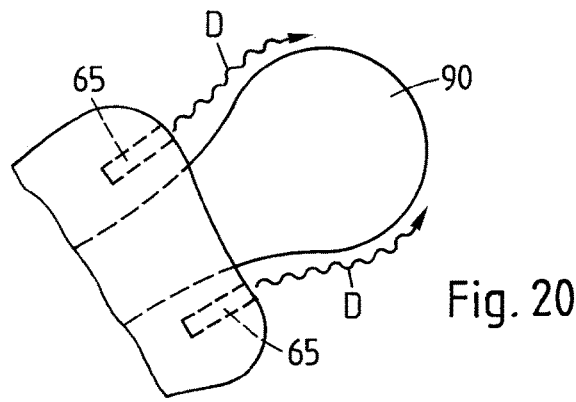

FIG. 20 shows a further application of the invention, wherein a drug, e.g. an antibiotic drug (drug delivery D), is delivered from drug delivery devices 65 according to the invention, which devices are implanted in the vicinity of an implanted endoprosthesis 90, wherein the endoprosthesis is partly implanted in a bone and partly protrudes from the bone to be adjacent to other tissues or further parts of endoprostheses. The devices are equipped for drug delivery on the accessible side of the bone in which they are implanted e.g. in the manner as described in combination with FIGS. 3, 4 and 6 and they deliver a drug along the surface of the prosthesis part protruding from the bone (e.g. prophylactic antibiotic treatment).

Figure 21:
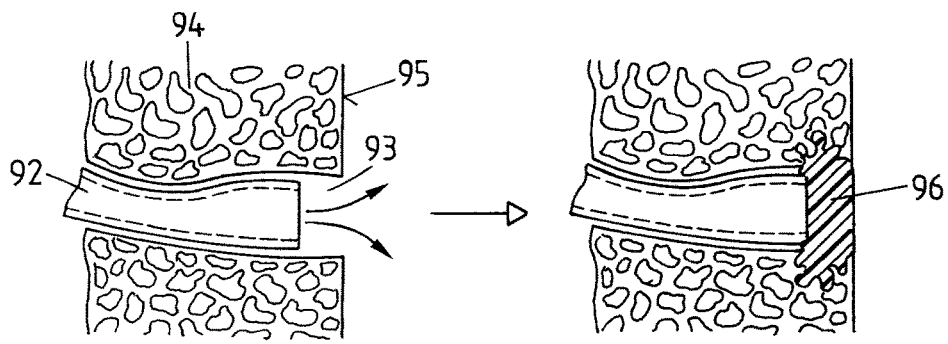

FIG. 21 shows a further application of the invention, wherein a closure element (as briefly described above in the context of FIG. 16) is used for sealing a blood vessel 92 (arteriole or venule) extending along a canal 93 within the trabecular structure 94 of canncellous bone and which is cut e.g. during bone surgery. Cutting through bone tissue may result in cutting through blood vessels of the named type. This may lead to a haemorrhage which is not easily stopped as the cut end of the blood vessel 92 is immediately retracted from the cut bone surface 95 into the bone tissue where it cannot be closed by being clamped or cauterized. However, as shown on the right hand side of FIG. 21, such haemorrhage can easily be stopped with the aid of a closure element 96 consisting of a thermoplastic, preferably resorbable material or carrying at least a ring of such a material around its circumference. Such a cover element is chosen to have a size and form adapted to the open end of the canal 93 as closely as possible and which is introduced into this canal end with the aid of e.g. a vibrating tool (e.g. sonotrode of an ultrasonic device, not shown) and at the same time is sealingly anchored in the canal wall near the cut end of the canal such stopping the haemorrhage. If, as illustrated in FIG. 21, the closure element is introduced into the canal 93 such that its proximal face is flush with the cut surface 95 of the bone tissue, the closure element 96 does not constitute any hindrance for further surgical steps at the cut bone surface 95.

Figure 22:
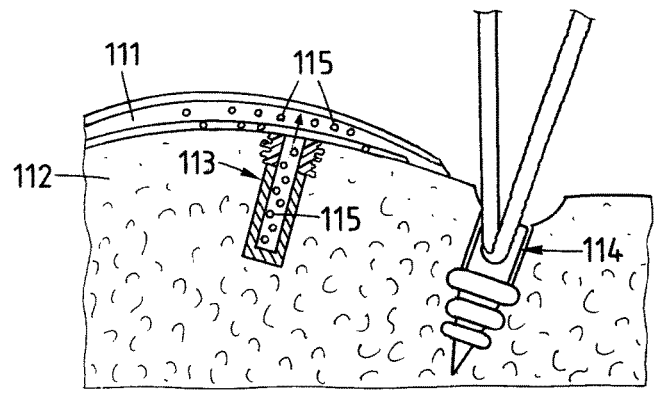
FIGS. 22 and 23 show further exemplary methods according to embodiments of the invention near a soft and hard tissue or tissue replacement material interface

FIG. 22 shows a further embodiment drug delivery device 113 suitable for drug delivery to the accessible side of the hard tissue/hard tissue replacement material 112 (e.g. bone or bone replacement tissue) into which it is implanted near or at a tissue interface 111/112 which is an interface of adjacent hard tissue/hard tissue replacement material 111 and soft tissue/soft tissue replacement material 112 interface such as a tendon/bone or ligament/bone interface for local delivery of a drug 115 promoting healing of the surrounding tissue e.g. after an injury or rupture of a ligament or tendon or during replacement surgery of a natural joint with a prosthesis. In other embodiments the drug delivery device implanted near or at such a tissue interface 111/112 is suitable for intra-osseous drug delivery and in yet further embodiments drug is delivered both into the bone tissue and at or near the tissue interface 111/112.

The one or more drug component 115 to be delivered by the drug delivery device 113 in this and other preferred embodiments of the invention are selected in particular from drugs promoting healing, in particular promoting growth, differentiation and/or regeneration and are also selected from antibiotic and anti-inflammatory drugs. Such drugs comprise both proteinaceous drugs like growth and differentiation factors e.g. the Bone Morphogenic Protein family (BMP 2, 6, 7, 12, 13), Insulin Growth Factor (e.g. IGF 1), Platelet Derived Growth Factor (PDGF), Growth and Differentiation Factor (e.g. GDF 5) etc. and also non-proteinaceous drugs including small molecules (e.g. biphosphonates).

In further embodiments of the method according to the invention the healing is promoted and/or palliative local treatment of a inflamed or injured tissue interface 111/112 as e.g. (partially) torn ligaments or inflamed tendons e.g. in chronic tendonitis is achieved by the implantation of drug delivery device 113 near the tendon/bone or ligament/bone interface i.e. at the interface or in the vicinity thereof. In preferred embodiments the drug delivery device 113 is implanted in minimally invasive procedures.

FIG. 22 additionally shows a suture anchor 114 which is used in preferred embodiments of the method according to the first or second aspect of the invention. Here a suture anchor 114 for attaching a suture to hard tissue 112 is also implanted in the vicinity of the tissue interface 111/112 such as a tendon/bone or ligament/bone interface for suturing the tendon or ligament into the hard tissue e.g. bone or bone replacement material. Shown in FIG. 22 is a preferred embodiment in which the drug delivery device is implanted into the hard tissue layer directly at the tissue interface 111/112, here underneath the layer of soft tissue. In further embodiments the drug delivery device is implanted in the vicinity of the tissue interface 111/112 rather than directly at the tissue interface 111/112. For example, in situations of limited space or where there is (residual) partial attachment of the soft tissue or in cases where an inflamed tissue interface region is treated the implantation of the drug delivery device 113 in the vicinity of the tendon/bone or ligament/bone interface may be preferable over an implantation into hard tissue or hard tissue replacement material directly at the tissue interface 111/112.

Such a method combining the implantation of two types of implants, i.e. one or more drug delivery device 113 and one or more suture anchor 114 for attaching a suture to a hard tissue, is generally applicable in surgical procedures, where tendons and ligaments need to be adapted to hard tissue (e.g. bone or bone replacement tissue). For example the method of combining these two types of implants is applicable for repair of a torn rotator cuff by implanting both a suture anchor 114 for attaching a suture which attaches a torn rotator cuff tendon to a humeral bone and implanting a drug delivery device 113 into the humeral bone. Further applications include attaching a torn Achilles' tendon by implanting a device for attaching a suture which attaches the plantaris, gastrocnemius (calf) and soleus muscles to the calcaneus (heel) bone and also implanting a drug delivery device implanted into the heel bone.

Figure 23:
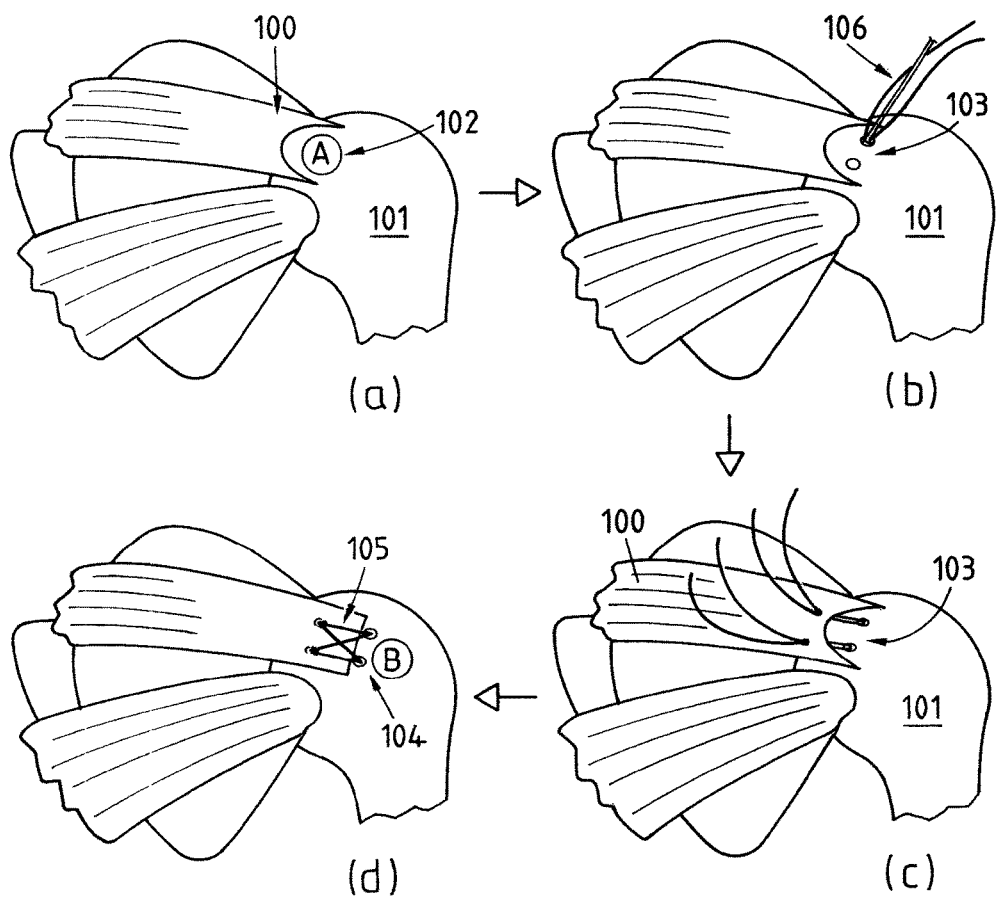

FIG. 23 illustrates a preferred method including the per se known knotless double row procedure for suturing a soft tissue to a hard tissue, using the example of reattaching a torn rotator cuff tendon 100 to humeral bone tissue 101 (or a corresponding endoprosthesis) in four successive phases (a), (b), (c) and (d). Phase (a) is before the repair operation and shows the location 102 in which reattachment is necessary. It also shows a region A of the bone tissue at the location in which reattachment is necessary and in which region A at the interface 111/112 at least one drug delivery device is implanted prior to the attachment steps in phase b) through d). After attachment of the soft tissue at the location 102, the region A comprising the implanted drug delivery device is at least partly covered by the soft tissue. In other embodiments at least one drug delivery device is implanted into the hard tissue prior, during or after any one of the phases a) through d), at a region B which lies in the vicinity of the location 102 where the attachment is necessary. Region B is different from region A in that it either lies outside of the soft tissue/hard tissue interface or in that it overlaps with interface 111/112 only to the extent that the region B during the surgical procedure is accessible without detaching connections between the soft and hard tissues or tissue replacement materials at the interface. In phase (b) two medial anchors 103 are anchored in the bone tissue, in locations to eventually be underneath the tendon 100, each one of the medial anchors 103 attaching at least one suture 4 to the bone tissue in a slideable manner. In phase (c) the end sections of each suture attached to one of the medial anchors is passed through the torn tendon 100 and by tensioning the sutures away from the tendon end (not shown), the latter is pulled over the medial anchors 103. In phase (d) two lateral anchors 104 are anchored in the bone tissue just beyond the edge of the tear, the row of lateral anchors 104 running about parallel to the row of medial anchors 103, the end sections of the sutures 106 being tensioned and locked with the aid of the lateral anchors 104 in a cross-wise manner, such that the two suture end sections held by one medial anchor 103 are locked by two different lateral anchors 104 such forming crossed suture bridges 105 between the row of medial anchors 103 and the row of lateral anchors 104.

One skilled in the art is capable without undue experimentation to combine features described for specific embodiments of device and method according to the invention in different ways and such creating further embodiments without departing from the scope of the invention.

EXAMPLES

Devices as illustrated in FIG. 7 and consisting of PLA were loaded with polylactide particles in which a few milligrams of methylene blue as a model drug of low molecular weight were integrated. The loaded devices were implanted as shown in FIG. 2, in tibial bone near the knee joint of sheep for intra-osseous delivery of the methylene blue. The tibial bone of sheep sacrificed 5 and 10 days after implantation was optically analyzed and the methylene blue was found in the cancellous bone around the implanted devices but none of it was detected in the periosteum or in any tissue adjoining the implantation site on the accessible side of the tibia bone.

The same experiment was carried out using devices substantially as illustrated in FIG. 3 and implanted as illustrated in FIG. 4 in tibial bone within the capsule of the knee joint of sheep for intra-articular delivery of the methylene blue. In the sacrificed sheep the articular cartilage of the knee joints was found to be blue, but no methylene blue was found in the cortical or cancellous bone surrounding the implant.

The results of the above described experiments show that the implant fully prevents a drug of small molecular weight to penetrate through the tibial cortical bone of sheep where the implant reaches through this cortical bone, i.e. drug delivery is fully restricted to either the non-accessible side or the accessible side of the cortical bone layer.

Devices as shown in FIG. 7 consisting of polylactide were loaded with granules of a bone substitute material containing a bone morphogenic protein (BMP) for intra-osseous delivery of the protein. Devices containing granules of the bone substitute material alone, i.e. without bone morphogenic protein were implanted as control. Implantation was carried out in subchondral tibial bone beneath the knee joint of sheep, wherein the depth of the opening provided for the implantation was greater than the axial length of the device such that after implantation of the device there was an empty space in the cancellous bone below the implanted device. In the sacrificed sheep new bone growth filled the hollow spaces below the loaded devices already after four weeks but hardly any was found underneath the control devices. No new bone growth or ossification of periosteum was found in the vicinity of the bone surface near the implantation site (accessible side of the cortical bone layer). This experiment shows that the thermal load to which the device is subjected on implantation is so small that the BMP being a very heat sensitive protein does not loose its efficacy. It further shows that, the same as the model drug methylene blue, the BMP is prevented from migrating from the one side of the cortical bone where it is delivered to the other side.

What is claimed is:

1. A device suitable for being implanted in a human or animal body and being equipped for signal delivery or signal acquisition within said body or an implantable device part of such a device, the device or device part further being suitable for fixation on or in hard tissue or corresponding replacement material:
    wherein the device or device part comprises a central portion and a circumferential portion and is configured to be inserted in an opening of a hard layer of the hard tissue or replacement material, the circumferential portion comprising a complete ring of a material having thermoplastic properties around the central portion and being liquefiable through application of energy to the ring or to device portions adjacent to the ring,
    the device or device part further comprising a signal delivery or signal acquisition portion,
    wherein the signal delivery or signal acquisition portion is arranged inside the central portion or reaches through the central portion, wherein the signal delivery or signal acquisition portion is accessible from a proximal side of the hard layer and is equipped for delivering a signal to a distal side of the hard layer or for acquiring a signal from the distal side of the hard layer or for both, and
    wherein the device or device part is equipped for transmission of energy to the ring or to the device portions adjacent to the ring for the purpose of liquefying at least part of the material having thermoplastic properties and to bring the material into contact with the hard tissue to form, on re-solidification, a complete sealing ring around the central portion.

2. The device or device part according to claim 1, wherein the complete ring of the material having thermoplastic properties is constituted by a ring part or a plurality of ring parts being capable of flowing together when liquefied to form the complete ring on implantation.

3. The device or device part according to claim 1, wherein the signal delivery or acquisition portion comprises at least one of an electronic or micromechanic device, an RFID-chip, a particle radiation source.

4. The device or device part according to claim 1 wherein the central portion consists of the material having thermoplastic properties.

5. The device or device part according to claim 1, wherein the central portion comprises a central septum element of a material having elastic properties.

6. A method of fixating a device suitable for being implanted in a human or animal body on or in hard tissue or corresponding replacement material in said body and being equipped for signal delivery or signal acquisition within said body or an implantable device part of such a device, the method comprising the steps of:
    providing the device or device part with a central portion and a circumferential portion and is configured to be inserted in an opening of a hard layer of the hard tissue or replacement material, the circumferential portion comprising a ring of a material having thermoplastic properties around the central portion and being liquefiable through application of energy to the ring or to device portions adjacent to the ring, and with a signal delivery or signal acquisition portion, wherein the signal delivery or signal acquisition portion is arranged inside the central portion or reaches through the central portion, wherein the signal delivery or signal acquisition portion is accessible from a proximal side of the hard layer and is equipped for delivering a signal to a distal side of the hard layer or for acquiring a signal from the distal side of the hard layer or for both,
    implanting the device or device part in an opening in a hard layer of the hard tissue or replacement material, the opening reaching through a hard tissue layer from an accessible side to a non accessible side thereof and comprising a mouth at least partly in a surface of the hard tissue or replacement material and a wall at least partly of the hard tissue or replacement material and further comprising a cross section at least partly adapted to said circumferential portion, by carrying out the steps of:
    positioning the device or device part relative to said opening such that the circumferential portion is in contact with the hard tissue or replacement material around the mouth of the opening and said ring extends at least partly around said opening in the vicinity of at least one of said wall and said surface,
    transmitting energy to said ring for a time sufficient to liquefy at least part of said material having thermoplastic properties and making the material having thermoplastic properties, to flow to form a complete ring and to contact the hard tissue or replacement material, and letting the liquefied material to re-solidify to constitute at least part of a sealing ring in sealing contact with said wall.

7. The method according to claim 6, wherein the step of transmitting energy comprises applying a sonotrode coupled to an active ultrasonic device to a proximal end of the device or device part and therewith transmitting ultrasonic vibratory energy to the device or device part and simultaneously pressing the device or device part deeper into the opening.

8. The method according to claim 6, wherein the hard layer is a cranial bone.

* * * * *